(12) United States Patent
Iwasawa

(10) Patent No.: US 10,921,571 B2
(45) Date of Patent: Feb. 16, 2021

(54) OBSERVATION OPTICAL SYSTEM, OBSERVATION IMAGING DEVICE, OBSERVATION IMAGING SYSTEM, IMAGE FORMING LENS SYSTEM, AND METHOD OF ADJUSTING OBSERVATION OPTICAL SYSTEM

(71) Applicant: Tamron Co., Ltd., Saitama (JP)

(72) Inventor: Yoshito Iwasawa, Saitama (JP)

(73) Assignee: Tamron Co., Ltd., Saitama (JP)

( * ) Notice: Subject to any disclaimer, the term of this patent is extended or adjusted under 35 U.S.C. 154(b) by 220 days.

(21) Appl. No.: 16/092,108

(22) PCT Filed: Jun. 30, 2016

(86) PCT No.: PCT/JP2016/069549
§ 371 (c)(1),
(2) Date: Oct. 8, 2018

(87) PCT Pub. No.: WO2017/195387
PCT Pub. Date: Nov. 16, 2017

(65) Prior Publication Data
US 2019/0339501 A1 Nov. 7, 2019

(30) Foreign Application Priority Data
May 13, 2016 (JP) .................. 2016-096756

(51) Int. Cl.
*G02B 21/02* (2006.01)
*G02B 21/36* (2006.01)
*G02B 13/00* (2006.01)

(52) U.S. Cl.
CPC .......... *G02B 21/02* (2013.01); *G02B 21/361* (2013.01); *G02B 13/002* (2013.01)

(58) Field of Classification Search
CPC ...... G02B 21/02; G02B 21/33; G02B 23/243; H01L 2924/00; G11B 7/1374
USPC ........................................ 359/661
See application file for complete search history.

(56) References Cited

U.S. PATENT DOCUMENTS

| 5,341,240 | A | 8/1994 | Broome |
| 5,457,576 | A | 10/1995 | Atkinson et al. |
| 6,252,722 | B1 * | 6/2001 | Kittaka ............... G02B 23/243 359/654 |
| 7,224,535 | B2 | 5/2007 | Neil |
| 9,041,848 | B2 | 5/2015 | Inoko |

(Continued)

FOREIGN PATENT DOCUMENTS

| CN | 101268399 A | 9/2008 |
| EP | 2899581 A1 | 7/2015 |

(Continued)

*Primary Examiner* — Mohammed A Hasan
(74) *Attorney, Agent, or Firm* — The Webb Law Firm

(57) ABSTRACT

A small observation optical system having a high resolution, an observation imaging device that includes the observation optical system, an observation imaging system, an image forming lens system, and a method of adjusting the observation optical system. The observation optical system includes an objective lens system G1 and an image forming lens system G2, sequentially from the observation object side, and the image forming lens system G2 forms an observation object image forms through the objective lens system G1, on an image plane IP of an image sensor, and satisfies predetermined condition.

21 Claims, 10 Drawing Sheets

(56) References Cited

U.S. PATENT DOCUMENTS

| | | |
|---|---|---|
| 2002/0085272 A1 | 7/2002 | Tomioka et al. |
| 2004/0021953 A1 | 2/2004 | Betensky et al. |
| 2012/0007972 A1* | 1/2012 | Uzawa ................ G02B 13/06 348/65 |
| 2015/0268453 A1 | 9/2015 | Oe et al. |
| 2015/0359422 A1* | 12/2015 | Igarashi ............. A61B 1/00163 600/135 |
| 2015/0362712 A1 | 12/2015 | Yabe |

FOREIGN PATENT DOCUMENTS

| | | |
|---|---|---|
| JP | 7146435 A | 6/1995 |
| JP | 1073762 A | 3/1998 |
| JP | 2002365558 A | 12/2002 |
| JP | 2006512595 A | 4/2006 |
| JP | 201429392 A | 2/2014 |
| JP | 2014157209 A | 8/2014 |
| JP | 2015179270 A | 10/2015 |
| WO | 2014045596 A1 | 3/2014 |

* cited by examiner

R2: L19~L28
R3: L29~L38

OBSERVATION OPTICAL SYSTEM, OBSERVATION IMAGING DEVICE, OBSERVATION IMAGING SYSTEM, IMAGE FORMING LENS SYSTEM, AND METHOD OF ADJUSTING OBSERVATION OPTICAL SYSTEM

CROSS-REFERENCE TO RELATED APPLICATIONS

This application is the United States national phase of International Application No. PCT/JP2016/069549 filed Jun. 30, 2016, and claims priority to Japanese Patent Application No. 2016-096756 filed May 13, 2016, the disclosures of which are hereby incorporated in their entirety by reference.

BACKGROUND OF THE INVENTION

Field of the Invention

The present invention relates to an observation optical system, an imaging device and the like for obtaining an observation image of an object, and in particular, to an observation optical system, an imaging device and the like which are suitable for observation of a minute object or interior observation of a narrow space.

Description of Related Art

In recent years, imaging devices, such as digital still cameras, have been widespread, and the performance and the number of pixels of a solid-state image sensor have been further improved. In recent years, the screen size and the number of pixels of an image output device, such as a monitor, have also been improved. With such improvements, an observation system has also been widespread that displays an object image obtained by an imaging device, on a large screen of an image output device, and allows many people to observe the details of the object image at the same time. For example, such an observation system is used when a minute object is observed through a microscope or the like or when the inside of a narrow space any person cannot enter is observed. The observation system uses a solid-state image sensor with the extremely high number of pixels. Consequently, further improvements in high quality and high resolution are required also for an optical system.

For example, an optical system described in Patent Literature 1 (Japanese Patent Laid-Open No. 10-73762) has been known as an optical system used for such an observation system. The optical system described in Patent Literature 1 includes an objective lens accommodated in a narrow cylindrical insertion portion. In the optical system described in Patent Literature 1, the reduction in size and increasing the wide angle of the objective lens are facilitated. The insertion portion can be inserted into the inside of a narrow space, such as the inside of a living organism. Accordingly, interior observation of such a narrow space can be favorably performed.

[Patent Literature 1] Japanese Patent Laid-Open No. 10-73762

Incidentally, increase in screen size and high-pixelization of the image output device in recent years has been advanced significantly. A solid-state image sensor supporting a full HD or higher resolution has been used. However, the optical system described in Patent Literature 1 supports a resolution nearly equivalent to a hi-vision resolution, but in the existing situation, an optical system that can support a solid-state image sensor having a higher-resolution is required.

In recent years, with increase in screen size and high-pixelization of the image output device, a large-sized solid-state image sensor having an image height of 8 mm or more has been used. However, in the optical system described in Patent Literature 1, it is assumed to use a small-sized solid-state image sensor having an image height of about 3.5 mm. Accordingly, if the optical system described in Patent Literature 1 is applied to a large-sized solid-state image sensor, the optical system should be increased in size, the size of the insertion portion is increased, and interior observation of the narrow space becomes difficult.

SUMMARY OF THE INVENTION

An object of the present invention is to provide a small observation optical system having a high resolution, an observation imaging device that includes the observation optical system, an observation imaging system, an image forming lens system, and a method of adjusting the observation optical system.

To solve the above problem, an observation optical system according to the present invention includes an objective lens system and an image forming lens system, sequentially from an observation object side, and the image forming lens system forms an observation object image formed through the objective lens system, on an image plane of an image sensor, and satisfies a following condition.

$$4000 < Y/P \times |\beta| < 32000 \quad (1)$$

where
Y: a length of half a diagonal length of the image plane,
P: a pixel pitch on the image plane, and
$\beta$: a lateral magnification of the image forming lens system.

To solve the above problem, an observation imaging device according to the present invention includes the observation optical system, and the image sensor arranged on an image side of the observation optical system, the image sensor converts the observation object image formed through the observation optical system into image data.

To solve the above problem, an observation imaging system according to the present invention includes the observation imaging device, and further includes an image processor part that electrically processes image data generated by the observation imaging device.

To solve the above problem, an image forming lens system according to the present invention is an image forming lens system for forming the observation object image formed through the objective lens system, on an image plane of an image sensor, and satisfies the following condition.

$$2.5 < |\beta| < 12.0 \quad (9)$$

where
$\beta$: a lateral magnification of the image forming lens system.

To solve the above problem, a method of adjusting the observation optical system according to the present invention is to reduce an amount of error occurring owing to production error in the observation optical system, by adjusting an air interval, or by decentering at least one lens among lenses included in the observation optical system.

According to the present invention, a small observation optical system having a high resolution, an observation imaging device that includes the observation optical system, an observation imaging system, an image forming lens system, and a method of adjusting the observation optical system, can be provided.

DESCRIPTION OF THE INVENTION

Figure 1:
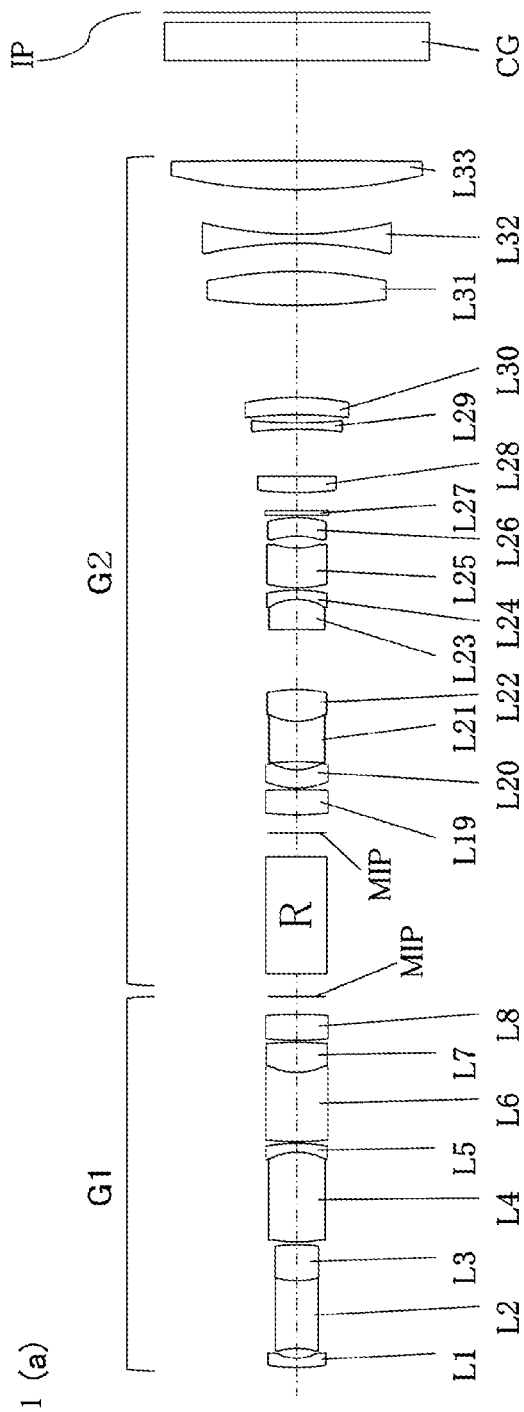
FIG. 1 is a lens sectional view of an observation optical system of example 1 according to the present invention at a time of focusing at infinity. Note that (a) shows the observation optical system where the configuration of a relay lens system is simplified, and (b) shows a specific configuration of the relay lens system (hereinafter, the same applies to lens sectional views).

Hereinafter, embodiments of an observation optical system, an image forming lens system, a method of adjusting the observation optical system, an observation imaging device, and an observation imaging system according to the present invention are sequentially described.
1. Observation Optical System
1-1. Lens Configuration First, an embodiment of the observation optical system according to the present invention is described. The observation optical system according to the present invention includes an objective lens system and an image forming lens system, sequentially from an observation object side, and is an observation optical system for causing the image forming lens system forms an observation object image formed through the objective lens system, on an image plane of an image sensor, and satisfies predetermined conditional expressions described later.

Here, the observation optical system includes at least one image forming plane between the observation object and the image plane of the image sensor. In the observation optical system, when the image forming plane arranged nearest to the object side is called a first intermediate image forming plane, the objective lens system is a lens system that includes lenses from the observation object side to the first intermediate image forming plane. Furthermore, in this specification, the first intermediate image forming plane indicates an image forming plane on which the observation object image is formed through the objective lens system, that is, the image forming plane of the objective lens system. In the observation optical system, the image forming lens system is a lens system that includes lenses between the first intermediate image forming plane and the image plane of the image sensor.

In the observation optical system, a primary image of the observation object image is formed on the first intermediate image forming plane through the objective lens system. The observation object image formed on the first intermediate image forming plane is re-formed on the image plane of the image sensor through the image forming lens system. As described above, by forming the primary image of the observation object image through the objective lens system, the observation optical system can be achieved that can support an image sensor having a high resolution and a high image height (for example, a large image sensor having an image height of 8 mm or more), without increasing the outer diameters of the lenses constituting the objective lens system arranged nearest to the observation object side. However, in the following description, for the sake of convenience, the image forming plane between the observation object and the image plane is called an intermediate image forming plane, and the observation object image formed on the intermediate image forming plane is called an intermediate object image, in some cases.

In the observation optical system, there is no problem if the intermediate image forming plane is flat or curved. However, in view of favorable aberration correction, a flat plane is preferable.

The observation optical system may include n (note that n is an integer of n≥1) intermediate image forming planes. The number (n) of intermediate image forming planes included in the observation optical system is not specifically limited. However, increase in the number (n) of intermediate image forming planes included in the observation optical system is not preferable in view of aberration correction. In view of forming an observation object image having a high resolution on the image plane of the image sensor, it is preferable that the number (n) of intermediate image forming planes included in the observation optical system be three or less, it is more preferable that the number be two or less, and it is most preferable that the number be one.

In a case where the observation optical system includes a first intermediate image forming plane, a second intermediate image forming plane, . . . , an n-th intermediate image forming plane, from the object side, it is assumed that the second intermediate image forming plane to the n-th intermediate image forming plane are included in the image forming lens system.

In a case where the observation optical system includes two or more intermediate image forming planes, a lens system made up of lenses arranged between the intermediate image forming planes is called a relay lens system. That is, a lens system made up of lenses arranged between the first intermediate image forming plane and the second intermediate image forming plane, a lens system made up of lenses arranged between the second intermediate image forming plane and the third image forming plane, . . . , and a lens system made up of lenses arranged between the (n−1) image forming plane and the n-th intermediate image forming plane are each called a relay lens system. In a case where the observation optical system includes two or more intermediate image forming planes, the image forming lens system includes one or more relay lens systems. In a case where the number of intermediate image forming planes is one, the image forming lens system does not include any relay lens systems.

In a case where the observation optical system includes multiple relay lens systems in the following embodiments and examples, the description is made exemplifying a configuration where multiple relay lens systems having the same configuration are arranged. However, the observation optical system according to the present invention is not limited thereto. For example, in the case where multiple relay lens systems are arranged, relay lens systems having different magnifications may be arranged, or relay lens systems having different lens arrangement may be arranged.

By including one or more relay lens systems in the image forming lens system, the optical path length of the observation optical system can be increased without increasing the outer diameters of the lenses constituting the objective lens system. In this case, a sufficient optical path length can be achieved even if size of the objective lens system is reduced. Accordingly, it becomes easy to insert the objective lens system into a narrow space that is long and thin, such as the inside of a living organism and to use it, and the inside of such a narrow space can be favorably observed. Note that the relay lens system is not aplanatic. Accordingly, too many number of relay lens systems included in the image forming lens system is not preferable because the image forming performance is reduced. In this view, it is more preferable that the number of relay lens systems included in the image forming lens system be one.

Furthermore, it is preferable that the image forming lens system include a focus group movable in the optical axis direction. It is preferable that in the observation optical system, the focus be achieved by moving the focus group included in the image forming lens system, in the optical axis direction, according to the distance to the observation object.

In an image sensor having a high resolution, the pixel pitch is small. Accordingly, to support such an image sensor having a high resolution, the F number (Fno) is required to be small in view of the diffraction limit of the observation optical system. Note that the focal depth is represented as Fno×2×P. If the focusing position deviates from the focal depth, the taken image is determined as a so-called out-of-focus image. Consequently, to achieve an observation optical system that can support an image sensor having a high resolution and a high image height, the focusing position is required to be accommodated in the focal depth even if the distance to the observation optical system varies. Accordingly, by providing the focus group in the image forming lens system, the focusing position can be adjusted according to the distance to the observation optical system. Consequently, an observation object image having a sharp outline without out-of-focus can be easily obtained.

1-2. Conditional Expressions

Hereinafter, preferable conditions that the observation optical system should satisfy are described.

1-2-1. Conditional Expression (1)

The observation optical system satisfies the following condition.

$$4000 < Y/P \times |\beta| < 32000 \qquad (1)$$

where

Y: the length of half a diagonal length of the image plane of the image sensor,

P: the pixel pitch on the image plane of the image sensor, and $\beta$: the lateral magnification of the image forming lens system.

The conditional expression (1) is an expression that defines the relationship between the size of the image sensor provided on the image side of the observation optical system, the pixel pitch, and the lateral magnification of the image forming lens system. If the conditional expression (1) is satisfied, a small observation optical system can be obtained that has a high resolution and can support a large image sensor having a large number of pixels. Furthermore, a bright optical system having a small F number can be achieved. Accordingly, the objective lens system suitable for interior observation of a narrow space having a low light intensity can be achieved. Furthermore, even when an intermediate object image formed through the objective lens system is enlarged through the image forming lens system and image-formed on the imaging plane of the image sensor, an observation object image having a sharp outline can be obtained.

On the contrary, if the numerical value of conditional expression (1) is the upper limit value or more, the lateral magnification of the image forming lens system is too large with respect to the number of pixels of the image sensor. In the case where the image forming lens system enlarges the intermediate object image, the aberrations are enlarged at the same time. Accordingly, to maintain a favorable image forming performance, the amount of aberration generated in the objective lens is required to be small. However, if the amount of aberration generated in the objective lens system is intended to be reduced, it is difficult to facilitate reduction in size of the objective lens system.

If the lateral magnification of the image forming lens system is too large, it is difficult to achieve a bright optical system having a small F number. This case is not preferable because the resolution performance of the high frequency component becomes low owing to the diffraction limit.

On the other hand, if the numerical value of the conditional expression (1) is the lower limit value or less, that is, if the lateral magnification of the image forming lens system is too small with respect to the number of pixels of the image sensor, it becomes difficult to facilitate reduction in size of the objective lens system for the sake of achieving the resolution that can support the image sensor having a large number of pixels.

To exert the above advantageous effect, it is preferable that the upper limit value of the conditional expression (1) be 28000, it is more preferable that the value be 25000, and it is further preferable that the value be 22000. Furthermore, it is preferable that the lower limit value of the conditional expression (1) be 5000, it is more preferable that the value be 6000, and it is further preferable that the value be 7000.

Here, the imaging plane of the image sensor means the imaging plane of the image sensor arranged on the image plane of the observation optical system. Note that in a case where multiple image sensors are arranged on the image plane with their imaging planes not overlapping with each other, and the optical path of the image forming lens system is split by a split prism and is projected onto the imaging plane of each image sensor, the multiple image sensors as a whole have a function equivalent to that in a case where one large image sensor is used. In such a case of using multiple image sensors, the imaging plane of the image sensor means the imaging plane of one large image sensor that can be regarded to be equivalent to the multiple image sensors. Note that the pixel pitch is defined as an interval between the pixel centers of pixels adjacent to each other on the imaging plane, and in a case where multiple image sensors are arranged by shifting pixels each other, the pixel pitch is defined as the pixel-shifting amount.

Preferably, in the observation optical system, the objective lens system includes at least one cemented lens including a lens having a positive refractive power and a lens having a negative refractive power which are cemented to each other, and the cemented surface has a negative refractive power. The objective lens system includes such a cemented lens, which can reduce the chromatic aberration occurring in the objective lens system. By satisfying the conditional expression (1), the observation optical system facilitates reduction in size of the objective lens system as described above. If the lateral magnification (0) of the image forming lens system is large, the longitudinal aberration occurring in the objective lens system is increased by the square of the lateral magnification of the image forming lens system, and the lateral aberration occurring in the objective lens system is increased by the factor of the lateral magnification of the image forming lens system. Accordingly, the objective lens system is configured to include at least one cemented lens described above, and the chromatic aberration to occur in the objective lens system is reduced, which can favorably obtain the advantageous effect of the conditional expression (1), and is preferable in view of improvement in performance and reduction in size.

1-2-2. Conditional Expression (2)

Preferably, the observation optical system satisfies the following condition.

$$50 < Y/P/Fno < 600 \quad (2)$$

where

Fno: the F number of the observation optical system.

The conditional expression (2) is an expression that defines the relationship between the size of the image sensor, the pixel pitch, and the F number (Fno) of the observation optical system. If the conditional expression (2) is satisfied, aberration correction can be favorably performed with a small number of lenses, and the small observation optical system having a high resolution can be easily obtained.

On the contrary, if the numerical value of the conditional expression (2) is the upper limit value or more, that is, if the F number of the observation optical system is too small with respect to the number of pixels of the image sensor, it is difficult to perform aberration correction favorably with a small number of lenses. For the sake of obtaining the observation optical system having a high resolution, it becomes difficult to reduce the size of the observation optical system. On the other hand, the numerical value of the conditional expression (2) is the lower limit value or less, that is, if the F number of the observation optical system is too small with respect to the number of pixels of the image sensor, it is not preferable because the resolution performance of the high frequency component is low owing to the diffraction limit.

To exert the above advantageous effect, it is preferable that the upper limit value of the conditional expression (2) be 500, it is more preferable that the value be 400, and it is further preferable that the value be 350. Furthermore, it is preferable that the lower limit value of the conditional expression (2) be 52, it is more preferable that the value be 55, and it is further preferable that the value be 60.

1-2-3. Conditional Expression (3)

The conditional expression (3) is an expression that defines the condition pertaining to the lens arranged nearest to the observation object side in the objective lens system. Before the description of the conditional expression (3), the refractive power of the lens is described. Preferably, in the observation optical system, the lens arranged on the most observation object side in the objective lens system has a negative refractive power. In a case where the lens arranged nearest to the observation object side in the objective lens system has a negative refractive power, increase in the field of view of the objective lens system is facilitated, and reduction in size of the outer diameters of the lenses constituting the objective lens system can be facilitated while allowing wide-range observation. Accordingly, the objective lens system suitable for interior observation of a narrow space can be achieved. At the same time, the field curvature and the coma can be favorably corrected. Accordingly, the observation optical system having a further high performance can be achieved.

Note that the lens arranged nearest to the observation object side in the objective lens system is only required to have a negative refractive power. The lens may be a single lens, or a cemented lens including multiple lenses cemented to each other, such as a cemented lens including a positive lens and a negative lens cemented to each other. In a case where at least one surface of the lens is aspherical, this case is preferable because the distortion aberration and the field curvature are further favorably corrected. In a case where a diffraction grating structure is provided on at least one surface of the lens, this case is preferable because the longitudinal chromatic aberration and the chromatic aberration of magnification can be further favorably corrected.

Preferably, in a case where the lens arranged nearest to the observation object side in the objective lens system has a negative refractive power, it is preferable to satisfy the following condition represented by the conditional expression (3).

$$-3.00 < fL1/ff < -0.80 \quad (3)$$

where fL1: the focal length of the lens arranged nearest to the observation object side in the objective lens system, and ff: the focal length of the objective lens system.

In a case where the lens arranged nearest to the observation object side in the objective lens system is a cemented lens including multiple single lenses cemented to each other, fL1 is the focal length of the cemented lens.

The conditional expression (3) is an expression that defines the ratio of the focal length of the lens arranged nearest to the observation object side in the objective lens system to the focal length of the objective lens system. If the conditional expression (3) is satisfied, the ratio of the focal length of this lens to the focal length of the objective lens system is within an appropriate range, and reduction in size of the objective lens system arranged nearest to the observation object side can be easily achieved. Furthermore, it is also effective in correcting the distortion aberration, the field curvature, and the coma.

On the contrary, if the numerical value of the conditional expression (3) is the upper limit value or more, that is, the focal length of the lens arranged nearest to the observation object side in the objective lens system is short with respect to the focal length of the objective lens system accordingly, and the amount of generation of the distortion aberration, the field curvature, the coma and the like increases. Consequently, it is not preferable in view of further increase in performance of the observation optical system. On the other hand, if the numerical value of the conditional expression (3) is the lower limit value or less, the focal length of the lens arranged nearest to the observation object side in the objective lens system increases with respect to the focal length of the objective lens system.

In this case, the lens having a larger outer diameter is required to be arranged nearest to the observation object side in the objective lens system. Consequently, it is difficult to facilitate reduction in size of the objective lens system, which is not preferable.

To exert the above advantageous effect, it is preferable that the upper limit value of the conditional expression (3) be −0.85, it is more preferable that the value be −0.90, it is further preferable that the value be −0.95, and it is most preferable that the value be −1.00. Furthermore, it is preferable that the lower limit value of the conditional expression (3) be −2.50, it is more preferable that the value be −2.00, and it is further preferable that the value be −1.80.

1-2-4. Conditional Expression (4)

Preferably, the observation optical system includes at least one lens that satisfies the following condition.

$$1.86 < Nd \qquad (4)$$

where

Nd: the refractive index for d-line.

The conditional expression (4) is an expression pertaining to at least any one lens included in the observation optical system. The lens satisfying the conditional expression (4) may be a lens that has a large refractive index and has a large refractive power, thus allowing the Petzval sum to be improved. Accordingly, by including at least one lens satisfying the conditional expression (4), further improvement in performance of the observation optical system is facilitated. Note that it is preferable that the observation optical system include at least one lens. The lens may be included in any of the objective lens system and the image forming lens system. The observation optical system may include multiple lens described above.

To exert the above advantageous effect, it is preferable that the lower limit value of the conditional expression (4) be 1.90, it is more preferable that the value be 1.91, it is further preferable that the value be 1.94, and it is most preferable that the value be 2.00.

In a case where the observation optical system includes the lens, it is preferable that the lens have a negative refractive power. The observation optical system forms the observation object image on the image plane of the image sensor. Accordingly, the observation optical system has a positive refractive power as a whole. Consequently, the negative refractive power included in the observation optical system is weaker than the positive refractive power included in the observation optical system. Accordingly, by adopting a lens having a negative refractive power as the lens satisfying the conditional expression (4), the Petzval sum can be further favorably achieved, and achievement of further improvement in performance of the observation optical system is further facilitated.

1-2-5. Conditional Expression (5)

Preferably, the observation optical system satisfies the following condition.

$$0.10 < |ff|/|f| < 0.45 \qquad (5)$$

where ff: the focal length of the objective lens system, and f: the composite focal length of the observation optical system.

The conditional expression (5) is an expression that defines the ratio of the focal length of the objective lens system to the absolute value of the composite focal length of the observation optical system. The conditional expression (5) represents the reciprocal of the lateral magnification (β) of the image forming lens system. If the conditional expression (5) is satisfied, even if the observation optical system for the image sensor having a high resolution and a high image height is adopted, reduction in size of the objective lens system is facilitated, and achievement of the observation optical system suitable for interior observation of a narrow space and the like is facilitated.

On the contrary, if the numerical value of the conditional expression (5) is the upper limit value or more, that is, if the lateral magnification of the image forming lens system is small, it is not preferable because it becomes difficult to facilitate reduction in size of the objective lens system for the sake of supporting the image sensor having a high resolution and a high image height. On the other hand, if the numerical value of the conditional expression (5) is the lower limit value or less, that is, if the lateral magnification of the image forming lens system is large, reduction in size of the objective lens system is facilitated even with the image sensor having a high resolution and a high image height being supported, but the F number of the observation optical system is large, and it is difficult to achieve a bright optical system. Furthermore, this case is not preferable because the resolution performance of the high frequency component becomes low owing to the diffraction limit.

To exert the above advantageous effect, it is preferable that the upper limit value of the conditional expression (5) be 0.40, it is more preferable that the value be 0.35, it is further preferable that the value be 0.32, and it is most preferable that the value be 0.30. Furthermore, it is preferable that the lower limit of the conditional expression (5) be 0.11, it is more preferable that the value be 0.12, and it is further preferable that the value be 0.15.

1-2-6. Conditional Expression (6)

In a case where the image forming lens system includes the relay lens system, it is preferable that the relay lens system satisfy the following condition.

$$0.9 < |\beta r| \qquad (6)$$

where

βr: the lateral magnification of the relay lens system.

The conditional expression (6) is an expression for defining the lateral magnification of the relay lens system. If the conditional expression (6) is satisfied, the lateral magnification of the relay lens system is in an appropriate range, the intermediate object image formed on the first intermediate image forming plane through the objective lens system can be favorably image-formed on the imaging plane of the image sensor through the image forming lens system including the relay lens system without much increasing the aberrations and without much reducing the F number.

On the contrary, if the numerical value of the conditional expression (6) is the lower limit value or less, the intermediate object image formed on the first intermediate image forming plane through the objective lens system is much reduced through the relay lens system. Accordingly, to support the image sensor having a high resolution and a high image height, the lateral magnification of the lens system arranged nearer to the image side than the relay lens system in the observation optical system, that is, the objective lens system, is required to be large. This case is not preferable in view of facilitating improvement in performance of the observation optical system because the aberrations increase and the F number decreases.

To exert the above advantageous effect, it is preferable that the lower limit value of the conditional expression (6) be 0.92, it is more preferable that the value be 0.95, and it is further preferable that the value be 0.99.

1-2-7. Conditional Expression (7)

The conditional expression (7) is an expression that defines the condition pertaining to the focus group of the observation optical system. As described above, it is preferable that in the observation optical system, the image forming lens system include the focus group. In a case where the image forming lens system includes the focus group, it is preferable that the focus group satisfy the following condition.

$$0.2<|\{(1-(\beta f\times\beta f)\}\times\beta s\times\beta s|<12.0 \quad (7)$$

where $\beta f$: the lateral magnification of the focus group, and $\beta s$: the composite lateral magnification of the lens group arranged nearer to the image plane side than the focus group.

The conditional expression (7) is an expression for defining the focus sensitivity of the focus group included in the image forming lens system. If the conditional expression (7) is satisfied, the amount of movement of the focus group for adjusting the focusing position is in an appropriate range, the observation object image having a sharp outline with the focus being on the object can be obtained, and the reduction in size of the observation optical system can be further facilitated.

On the contrary, the numerical value of the conditional expression (7) is the upper limit value or more, the amount of movement of the focus group in the case of adjusting the positional deviation of the focusing position is too large. Consequently, a quick focusing operation becomes difficult, and it is not preferable in view of facilitating improvement in performance of the observation optical system. If the amount of movement of the focus group is large, the size of a drive mechanism for driving the focus group is also increased. Accordingly, it is not preferable because it becomes difficult to facilitate reduction in size of the observation optical system. On the other hand, if the numerical value of the conditional expression (7) is the lower limit value or less, only a slight amount of movement of the focus group in the case of adjusting the positional deviation of the focusing position is required. Consequently, it is advantageous for a quick focusing operation. However, it is not preferable because the positional control of the focus group is required to be performed with high accuracy.

To exert the above advantageous effect, it is preferable that the upper limit value of the conditional expression (7) be 10.0, it is more preferable that the value be 8.0, and it is further preferable that the value be 6.0. Furthermore, it is preferable that the lower limit of the conditional expression (7) be 0.3, it is more preferable that the value be 0.5, and it is further preferable that the value be 0.7.

1-2-8. Conditional Expression (8)

Preferably, in the observation optical system, the lens arranged nearest to the observation object side in the objective lens system satisfies the following condition.

$$0.70<CrL1r/f<2.50 \quad (8)$$

where $CrL1r$: the curvature radius of the image side surface of the lens arranged nearest to the observation object side in the objective lens system.

The conditional expression (8) is an expression pertaining to the ratio of the curvature radius of the image side surface of the lens arranged nearest to the observation object side in the objective lens system to the focal length of the objective lens system. If the conditional expression (8) is satisfied, the image side surface of the lens arranged nearest to the observation object side in the objective lens system is a surface that is concave to the image plane side and has an appropriate curvature. As a result, the amounts of generation of the field curvature and the coma can be suppressed, and the improvement in performance and reduction in size of the observation optical system can be facilitated.

On the contrary, if the numerical value of the conditional expression (8) is the upper limit value or more, the image side surface of the lens arranged nearest to the observation object side in the objective lens system is a surface that is concave to the observation object and has a small curvature. Accordingly, for the sake of increasing the wide angle of the observation optical system to allow wide-range observation, the outer diameters of the lenses constituting the objective lens system are required to be increased, which is not preferable to facilitate reduction in size of the observation optical system. On the other hand, if the numerical value of the conditional expression (8) is the lower limit value or less, the image side surface of the lens arranged nearest to the observation object side in the objective lens system is a surface that is concave toward the observation object and has a large curvature. Accordingly, the amounts of generation of the field curvature and the coma increase, and correction of these amounts becomes difficult, which is not preferable in view of facilitating improvement in performance of the observation optical system.

To exert the above advantageous effect, it is preferable that the upper limit value of the conditional expression (8) be 2.30, it is more preferable that the value be 2.10, and it is further preferable that the value be 1.90. Furthermore, it is preferable that the lower limit of the conditional expression (8) be 0.75, it is more preferable that the value be 0.80, and it is further preferable that the value be 0.90.

2. Image Forming Lens System

Next, the image forming lens system according to the present invention is described. The image forming lens system according to the present invention is a lens system for forming the observation object image formed through the objective lens system, on the image plane of the image sensor, and satisfies the following condition. Note that the image forming lens system may be an image forming lens system constituting the observation optical system according to the present invention, or a lens system for forming the observation object image formed through the objective lens system included in the observation optical system according to the present invention, on the image plane of the image sensor.

$$2.5<|\Theta|<12.0 \quad (9)$$

where $\beta$: the lateral magnification of the image forming lens system.

The conditional expression (9) is an expression that defines the lateral magnification of the image forming lens system. If the conditional expression (9) is satisfied, the observation object image (intermediate object image) formed through the objective lens system can be favorably formed on the image plane of the large image sensor having a large number of pixels. Accordingly, the observation optical system that includes the image forming lens system can be configured as a small observation optical system having a high resolution. Furthermore, a bright optical system having a small F number can be achieved. Accordingly, reduction in size of the objective lens system can be facilitated, and the objective lens system can be configured as a small lens system suitable for interior observation of a narrow space having a low light intensity.

On the contrary, if the numerical value of conditional expression (9) is the upper limit value or more, that is, the lateral magnification of the image forming lens system is too large, when the image forming lens system enlarges the intermediate object image, the aberrations are enlarged at the same time. Accordingly, to maintain a favorable image forming performance, the amount of aberration generated in the objective lens system is required to be small. However, if the amount of aberration generated in the objective lens system is intended to be reduced, it is difficult to facilitate reduction in size of the objective lens system.

If the lateral magnification of the image forming lens system is too large, it is difficult to achieve a bright optical system having a small F number. This case is not preferable because the resolution performance of the high frequency component becomes low owing to the diffraction limit.

On the other hand, if the numerical value of the conditional expression (9) is the lower limit value or less, that is, if the lateral magnification of the image forming lens system is too small, it becomes difficult to facilitate reduction in size of the objective lens system for the sake of achieving the resolution that can support the image sensor having a large number of pixels.

To exert the above advantageous effect, it is preferable that the upper limit value of the conditional expression (9) be 10.0, it is more preferable that the value be 9.0, and it is further preferable that the value be 8.0. Furthermore, it is preferable that the lower limit of the conditional expression (9) be 2.8, it is more preferable that the value be 3.0, and it is further preferable that the value be 3.3.

3. Method of Adjusting Observation Optical System

Next, a method of adjusting an observation optical system according to the present invention is described. The method of adjusting an observation optical system according to the present invention is characterized by reducing the amounts of error occurring owing to the production error by adjusting the air interval in the observation optical system.

The image sensor with a high resolution has a small pixel pitch. Consequently, the focal depth is shallow, and the diameter of an allowable circle of confusion is small. In such an image sensor having a high resolution, the permissible amount of aberration required for the observation optical system is small. The objective lens system and the image forming optical system are each made up of multiple lenses. The aberrations occur owing to the error caused in a case of lens processing and lens frame processing and a case of assembling the lens to a lens frame. According to the aberrations caused by such error, reduction in image quality of the observation object image formed on the imaging plane occurs. Accordingly, the air interval between lenses included in the observation optical system, such as the interval between lenses included in the objective lens system or the image forming lens system, or the interval between the objective lens system and the image forming lens system, is adjusted to reduce the amounts of error caused by the production error, thereby allowing the observation optical system having a high performance to be obtained.

Here, the amounts of error caused by the production error are the back focus error, the spherical aberration, the field curvature, the chromatic aberration and the like. Furthermore, the adjustment of the air interval is to change the air interval from its design value in a case without consideration of the production error. The air interval between freely selected lenses among the lenses constituting the observation optical system may be adjusted. The adjusting position, the number of lenses to be adjusted, the adjusting method, and the number of adjusting times can be determined arbitrarily.

The method of adjusting the observation optical system according to the present invention is to reduce the amounts of error occurring owing to the production error by decentering at least one lens.

As with the case of adjusting the air interval, decentering of at least one lens among the lenses included in the observation optical system can reduce the amounts of error occurring owing to the production error, and obtain the observation optical system having a high performance.

Here, the amounts of error caused by the production error is the amount of decentering error caused by the production error, and more specifically, the axial coma aberration, one-side blurring, image height error, color shift and the like. To decenter at least one lens means to incline and the like of at least one lens among the lenses constituting the observation optical system with respect to the optical axis. The position of the lens to be decentered, the number of adjusted lenses to be decentered, the decentering method, the number of decentering times, the center of rotation of the lens during decentering and the like can be determined arbitrarily.

4. Observation Imaging Device

Next, the observation imaging device according to the present invention is described. The observation imaging device according to the present invention includes the observation optical system according to the present invention, and the image sensor on the image side of the observation optical system, and causes the image sensor to convert the observation object image formed through the observation optical system into image data.

Here, the image sensor is not specifically limited, and may be a solid-state image sensor, such as a CCD (Charge Coupled Device) sensor or a CMOS (Complementary Metal Oxide Semiconductor) sensor. The resolution and the size of the solid-state image sensor are not specifically limited. As the observation optical system according to the present invention is suitable for a solid-state image sensor having a high resolution and a high image height, it is preferable that the solid-state image sensor have a full HD or higher resolution. It is more preferable that the resolution be 4K or higher. It is further preferable that the resolution be 8K or higher.

The observation imaging device may be configured as a digital still camera that obtains a still image, or configured as a digital video camera that obtains a moving image. The observation optical system according to the present invention has a high resolution. Consequently, this system is suitable as an observation imaging device for observing a minute object, such as a microscopic imaging device. The observation optical system according to the present invention can be configured so that the objective lens system arranged nearest to the observation object side can have a significantly small size. Consequently, for example, this system is also suitable as an observation imaging device for interior observation of a narrow space of the inside of a living organism or the like which a person cannot directly access. Furthermore, the observation imaging device may be a lens-fixed observation imaging device where the observation optical system is fixed in the housing, or an interchangeable lens imaging device where the whole or a part of the observation optical system (e.g., the objective lens system etc.) is detachable.

5. Observation Imaging System

Next, the observation imaging system according to the present invention is described. The observation imaging system according to the present invention is an observation imaging system that includes the observation imaging device according to the present invention, and further includes an image processor part that electrically processes image data pertaining to the observation object image generated by the observation imaging device.

The observation imaging system may include an image output device, such as a monitor. Preferably, this system is an observation system that outputs, to the image output device, the image data pertaining to the observation object image obtained by the observation imaging device, and allows many people to observe the details of the observation object image at the same time.

In a case where increase in field of view and reduction in size are achieved in the observation optical system according to the present invention, a distortion of an image form tends to occur. Accordingly, the observation imaging system is provided with the image processor part that electrically processes the distortion of the image form in the image data, thereby allowing the image output device or the like to output the observation object image having a small distortion of the image form. Preferably, the image processor part includes: a storage part that preliminarily stores therein correction data for correcting the distortion of the image form; an operation processor part (CPU) that associates the image data obtained in the observation imaging device with the correction data, and corrects the image data.

Here, it is preferable that the image processor part electrically process data pertaining to the distortion aberration among the image data pertaining to the observation object image obtained by the observation imaging device. Provided that the image processor part can electrically process the data pertaining to the distortion aberration, the image processor part can generate image data having small distortion aberration even if the lens arranged nearest to the observation object side is provided with the strong negative refractive power for the sake of increase the wide angle of the observation optical system through arranging the lens having negative refractive power nearest to the observation object side in the objective lens system. Accordingly, the small lens having a strong negative refractive power can be arranged nearest to the observation object side. The increase the wide angle and reduction in size of the observation optical system can be facilitated, and the image output device or the like is allowed to display the observation object image without distortion.

Furthermore, it is preferable that the image processor part electrically process data pertaining to the chromatic aberration of magnification among the image data pertaining to the observation object image obtained by the observation imaging device. If the image processor part can electrically process the data pertaining to chromatic aberration of magnification, the image output device is allowed to display the observation object image having small chromatic aberration. Accordingly, the number of lenses constituting the observation optical system can be reduced, and reduction in size of the observation optical system is facilitated.

Next, the present invention is specifically described, with examples being represented. Note that the present invention is not limited to the following examples. An optical system in each example described later is an observation optical system serving as an imaging optical system used for an imaging device (optical device), such as a digital camera and a video camera, and more specifically, can be favorably applied to a microscope, and an observation imaging device for interior observation of a narrow space. In each lens sectional view, the left indicates the observation object side (object side) and the right indicates the image plane side on the diagram.

Example 1

(1) Configuration of Observation Optical System

FIG. 1 shows a lens sectional view showing the lens configuration of an observation optical system according to example 1 of the present invention at a time of focusing at infinity. The observation optical system includes, from the observation object side: an objective lens system G1; and an image forming lens system G2 including a relay lens system R. In the observation optical system, an intermediate object image is formed on a first intermediate image forming plane MIP through the objective lens system G1. In the image forming lens system G2, the intermediate object image is formed on a second intermediate image forming plane MIP through the relay lens system R, and then image-formed on an image plane IP of the image sensor. The image forming lens system G2 includes not only the relay lens system R but also a focus group that moves toward the object side along the optical axis during focusing from an infinity object to a close object. In FIG. 1(a), the relay lens system R is represented as a block R. FIG. 1(b) shows the lens configuration of the relay lens system R. Elongated lines that are orthogonal to the optical axis and indicated on the observation object side and the image plane side of the relay lens system R are the first intermediate image forming plane MIP and the second intermediate image forming plane MIP, respectively, sequentially from the observation object side. In FIG. 1(a), "CG" is a cover glass or the like. These points are the same also in the other example. Accordingly, the description thereof is hereinafter omitted.

The objective lens G1 includes, from the observation object side: a negative meniscus lens L1 with the concave surface being oriented toward the image plane side; a cemented lens including a biconcave-shaped negative lens L2 and a biconvex-shaped positive lens L3 cemented to each other; an aperture regulation surface S for defining the maximum aperture; a cemented lens including a biconvex-shaped positive lens L4 and a negative meniscus lens L5 with the concave surface being oriented toward the object side; a cemented lens including a negative meniscus lens L6 with the concave surface being oriented toward the image plane side and a biconvex-shaped positive lens L7 cemented to each other; and a biconvex-shaped positive lens L8.

The image forming lens system G2 includes, sequentially from the observation object side: a relay lens system R; a biconvex-shaped positive lens L19; a negative meniscus lens L20 with the concave surface being oriented toward the image plane side; a cemented lens including a biconcave-shaped negative lens L21 and a biconvex-shaped positive lens L22 cemented to each other; a cemented lens including a positive meniscus lens L23 with the convex surface being oriented toward the image plane side and a negative meniscus lens L24 with the concave surface being oriented toward the object side which are cemented to each other; a negative meniscus lens L25 with the concave surface being oriented toward the image plane side; a negative meniscus lens L26 with the concave surface being oriented toward the object side; a parallel plate L27; a positive lens L28 with the convex surface being oriented toward the object side; a biconcave-shaped negative lens L29; a positive meniscus lens L30 with the convex surface being oriented toward the image plane side; a biconvex-shaped positive lens L31; a biconcave-shaped negative lens L32; and a biconvex-shaped positive lens L33.

As shown in FIG. 1(b), the relay lens system R includes, sequentially from the observation object side: a biconvex-shaped positive lens L9; a cemented lens including a biconcave-shaped negative lens L10 and a biconvex-shaped positive lens L11 cemented to each other; a cemented lens including a biconcave-shaped negative lens L12 and a biconvex-shaped positive lens L13 cemented to each other; a cemented lens including a biconvex-shaped positive lens L14 and a biconcave-shaped negative lens L15 cemented to each other; a cemented lens including a biconvex-shaped positive lens L16 and a biconcave-shaped negative lens L17 cemented to each other; and a biconvex-shaped positive lens L18.

In the image forming lens system G2, the biconvex-shaped positive lens L31 is a focus group that moves toward the object side along the optical axis during focusing from an infinity object to a close object.

In this example, the image forming lens system G2 includes one relay lens system R. This example may have a configuration including multiple relay lens systems R. If the number of relay lens systems R included in the image forming lens system G2 is increased, the optical path length of the observation optical system can be increased. Consequently, the observation optical system suitable for interior observation of a narrow space that is long and thin can be obtained.

If the field curvature occurs owing to production error in this case, the occurring field curvature can be reduced by, for example, moving the relay lens system R in the optical axis direction.

If the one-side blurring occurs owing to production error, for example, the occurring one-side blurring can be reduced by integrally moving L32 and L33 included in the image forming lens system G2 in the direction perpendicular to the optical axis.

In this example, it is preferable that the pixel pitch P on the image plane IP of the image sensor range from 2 to 8 μm. The observation optical system of this example is also applicable to image sensors with pitches out of this range.

(2) Numerical Value Example

Next, numerical value examples where specific numerical values of the observation optical system are applied are described. Lens data on the observation optical system of this example is shown in Tables 1 and 2. In Tables 1 and 2, "Surface number" indicates the order of the lens surface counting from the object side, "r" indicates the curvature radius of a lens surface, "d" indicates a distance between lens surfaces on the optical axis, "n" indicates the refractive index for d-line (wavelength $\lambda$=587.6 nm), and "v" indicates the Abbe number for d-line. "S" shown in the next field of the surface number indicates the aperture regulation surface. In each table, every length unit is "mm", and every unit of angle of view is "°". Here, in Table 1, no glass material is listed in fields with surface numbers "1" and "2". However, in the observation optical system shown in FIG. 1, for the sake of protecting the lens L1 arranged nearest to the observation object side, a cover glass may be inserted on the observation object side of the lens L1. The items on the lens data are analogous in each table presented in the other examples. Accordingly, the description is hereinafter omitted.

Table 3 shows variable intervals on the optical axis, a specification table, and the focal length of each lens system/group, in the observation optical system. The variable interval indicates the distance between lens surfaces at a time of focusing at infinity and at observation distances of 10, 5, 2.5 and 1 cm. In the specification table, "f" is the focal length (mm) of the observation optical system at a time of focusing at infinity, "Fno." is the F number of the optical system, and "Optical overall length" is the optical overall length of the optical system and is the distance (mm) from the first surface to the image plane. Furthermore, "ω" is the half image viewing angle (°) of the relevant optical system, and "Y" is the image height (mm) of the optical system. In the focal length of each lens system/group, "Objective lens system" is the focal length of the objective lens system G1, "Relay lens system" is the focal length of the relay lens system R, "Front side lens group" is the focal length of a front side lens group made up of lenses arranged between the relay lens system R and the focus group, "Focus group" is the focal length of the focus group, "Rear side lens group" is the focal length of a rear lens group made up of lenses arranged between the focus side group and the image plane, and "Image forming lens system" is the focal length of the image forming lens system G2. "Surface number" indicates the surface number included in each lens system/group. Furthermore, the numerical values of conditional expressions (1) to (9) are shown in Table 18. The items on these tables are analogous in each table presented in the other examples. Accordingly, the description is hereinafter omitted.

Figure 2:
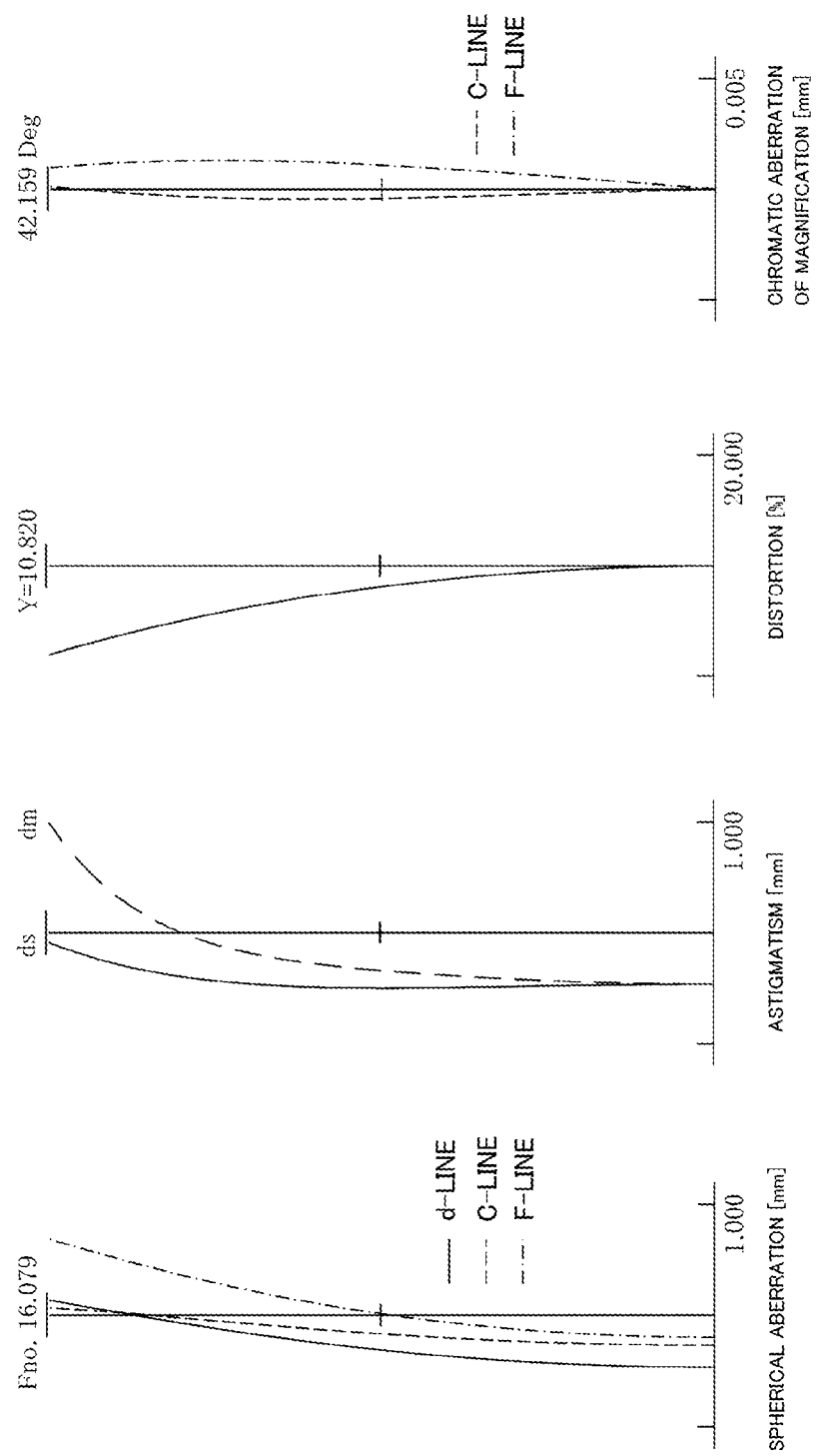
FIG. 2 is a spherical aberration diagram, an astigmatism diagram, a distortion aberration diagram, and a chromatic aberration of magnification diagram of the observation optical system according to example 1 at a time of focusing at infinity.

FIG. 2 shows longitudinal aberration diagrams of the optical system at a time of focusing at infinity. Each longitudinal aberration diagram shows, sequentially from the left on the diagram, the spherical aberration, astigmatism, distortion aberration, and chromatic aberration of magnification. In the diagram showing the spherical aberration, the ordinate axis indicates the ratio to the maximum aperture and the abscissa axis indicates the defocus, a solid line indicates the spherical aberration for d-line (wavelength $\lambda$=587.6 nm), a broken line indicates that for C-line (wavelength $\lambda$=656.3 nm), and a chain line indicates that for F-line (wavelength $\lambda$=486.1 nm). In the diagram showing the astigmatism, the ordinate axis indicates the image height and the abscissa axis indicates the defocus, a solid line indicates the sagittal image plane for d-line (ds), and a broken line indicates a meridional image plane for d-line (dm) In the diagram showing the distortion aberration, the ordinate axis indicates the image height and the abscissa axis indicates the distortion aberration (%). In the diagram showing the chromatic aberration of magnification, the ordinate axis indicates the angle of view and the abscissa axis indicates the chromatic aberration of magnification, a broken line indicates the chromatic aberration of magnification for C-line (wavelength $\lambda$=656.3 nm) with respect to d-line (wavelength $\lambda$=587.6 nm), and a chain line indicates the chromatic aberration of magnification for F-line (wavelength $\lambda$=486.1 nm) with respect to d-line (wavelength $\lambda$=587.6 nm).

The items on these diagrams are analogous in each longitudinal aberration diagram presented in the other examples. Accordingly, the description is hereinafter omitted.

TABLE 1

| Surface number | r | d | n | ν | Effective diameter |
|---|---|---|---|---|---|
| Object surface | ∞ | d0 | | | |
| 1 | ∞ | 0.0000 | | | 2.54 |
| 2 | ∞ | 0.0000 | | | 2.54 |
| 3 | 12.4000 | 1.0000 | 1.8830 | 40.81 | 2.34 |
| 4 | 2.7000 | 1.0665 | | | 1.65 |
| 5 | −4.4000 | 7.4300 | 1.8042 | 46.50 | 1.59 |
| 6 | 4.4000 | 3.9400 | 1.8467 | 23.78 | 1.74 |
| 7 S | −13.7000 | 0.3000 | | | 1.77 |
| 8 | 7.0100 | 9.8300 | 1.5688 | 56.04 | 1.84 |
| 9 | −3.8600 | 1.0000 | 1.8467 | 23.78 | 2.29 |
| 10 | −9.3600 | 0.1702 | | | 2.50 |
| 11 | 19.2000 | 7.6200 | 1.8467 | 23.78 | 2.53 |
| 12 | 4.0000 | 3.3100 | 1.4970 | 81.61 | 2.22 |
| 13 | −26.0000 | 0.2107 | | | 2.49 |
| 14 | 17.4000 | 2.8600 | 1.8467 | 23.78 | 2.55 |
| 15 | −21.7500 | 2.0004 | | | 2.54 |
| 16 | ∞ | 0.0000 | | | 2.36 |
| 17 | ∞ | 2.0076 | | | 2.36 |
| 18 | 18.8300 | 10.0000 | 1.9229 | 20.88 | 2.64 |
| 19 | −18.8300 | 0.2000 | | | 2.55 |
| 20 | −25.6000 | 14.5200 | 1.9037 | 31.32 | 2.52 |
| 21 | 5.8760 | 3.1900 | 1.8042 | 46.50 | 2.20 |
| 22 | −9.5400 | 0.7721 | | | 2.21 |
| 23 | −6.6300 | 1.0200 | 1.6989 | 30.05 | 2.08 |
| 24 | 5.8760 | 3.2600 | 1.7440 | 44.90 | 2.24 |
| 25 | −10.8000 | 0.2000 | | | 2.49 |
| 26 | ∞ | 0.0000 | | | 2.19 |
| 27 | ∞ | 0.2000 | | | 2.49 |
| 28 | 10.8000 | 3.2600 | 1.7440 | 44.90 | 2.49 |
| 29 | −5.8760 | 1.0200 | 1.6989 | 30.05 | 2.31 |
| 30 | 6.6300 | 0.7721 | | | 2.17 |
| 31 | 9.5400 | 3.1900 | 1.8042 | 46.50 | 2.27 |
| 32 | −5.8760 | 14.5200 | 1.9037 | 31.32 | 2.23 |
| 33 | 25.6000 | 0.2000 | | | 2.63 |
| 34 | 18.8300 | 10.0000 | 1.9229 | 20.88 | 2.66 |
| 35 | −18.8300 | 2.0076 | | | 2.70 |

TABLE 2

| Surface number | r | d | n | ν | Effective diameter |
|---|---|---|---|---|---|
| Object surface | ∞ | d0 | | | |
| 36 | ∞ | 0.0000 | | | 2.40 |
| 37 | ∞ | 2.0000 | | | 2.40 |
| 38 | 19.1300 | 2.6900 | 1.8061 | 33.27 | 2.56 |
| 39 | −130.7000 | 0.2000 | | | 2.57 |
| 40 | 4.5900 | 2.0500 | 1.9229 | 20.88 | 2.56 |
| 41 | 3.5000 | 0.8908 | | | 1.97 |
| 42 | −16.8350 | 4.4300 | 1.8467 | 23.78 | 1.97 |
| 43 | 4.0000 | 3.4800 | 1.8042 | 46.50 | 2.26 |
| 44 | −8.6300 | 6.6211 | | | 2.43 |
| 45 | −59.1000 | 3.2600 | 1.8052 | 25.46 | 2.00 |
| 46 | −3.5300 | 1.0200 | 1.8340 | 37.35 | 2.26 |
| 47 | −9.6100 | 0.3000 | | | 2.43 |
| 48 | 7.1300 | 4.3600 | 1.9229 | 20.88 | 2.44 |
| 49 | 4.0000 | 1.3212 | | | 1.74 |
| 50 | −4.4800 | 2.0000 | 1.4970 | 81.61 | 1.84 |
| 51 | −7.3700 | 0.3000 | | | 2.38 |
| 52 | ∞ | 0.5000 | 1.9108 | 35.25 | 2.54 |
| 53 | ∞ | 1.0000 | | | 2.60 |
| 54 | ∞ | 0.0000 | | | 2.84 |
| 55 | ∞ | 1.0000 | | | 2.84 |
| 56 | 19.5400 | 1.7700 | 1.8830 | 40.81 | 3.13 |
| 57 | ∞ | 5.1949 | | | 3.19 |
| 58 | −24.7300 | 0.7000 | 1.8052 | 25.46 | 3.57 |
| 59 | 24.7300 | 0.8667 | | | 3.71 |
| 60 | −27.7000 | 1.9200 | 1.8042 | 46.50 | 3.82 |
| 61 | −16.8350 | d61 | | | 4.24 |
| 62 | 42.3300 | 3.7300 | 1.4970 | 81.61 | 7.07 |
| 63 | −25.6100 | d63 | | | 7.28 |
| 64 | −24.4000 | 1.0000 | 1.6034 | 38.01 | 7.30 |
| 65 | 24.4000 | 4.8439 | | | 7.72 |
| 66 | 33.3000 | 3.2500 | 2.0007 | 25.46 | 10.23 |
| 67 | −385.4000 | 11.0000 | | | 10.27 |
| 68 | ∞ | 4.2000 | 1.5168 | 64.20 | 10.68 |
| 69 | ∞ | 1.0000 | | | 10.80 |
| 70 | ∞ | 0.0000 | | | 10.86 |

TABLE 3

[Variable interval]

| | | | | | |
|---|---|---|---|---|---|
| d0 | ∞ | 100.0000 | 50.0000 | 25.0000 | 10.0000 |
| d61 | 10.1954 | 9.0340 | 7.9844 | 6.1372 | 1.7988 |
| d63 | 3.1095 | 4.2710 | 5.3205 | 7.1678 | 11.5061 |

[Specification table]

| | |
|---|---|
| f | 13.8270 |
| Fno. | 16.1220 |
| Optical overall length | 201.3610 |
| ω | 42.1590 |
| Y | 10.8200 |

[Focal length of each lens system/group]

| | Surface number | Focal length |
|---|---|---|
| Objective lens system | 3-16 | 3.149 |
| Relay lens system | 18-36 | −208.119 |
| Front side lens group | 37-61 | 9.394 |
| Focus group | 62-63 | 32.607 |
| Rear side lens group | 64-67 | −115.756 |
| Image forming lens system | 18-67 | −23.960 |

Example 2

(1) Configuration of Observation Optical System

Figure 3:
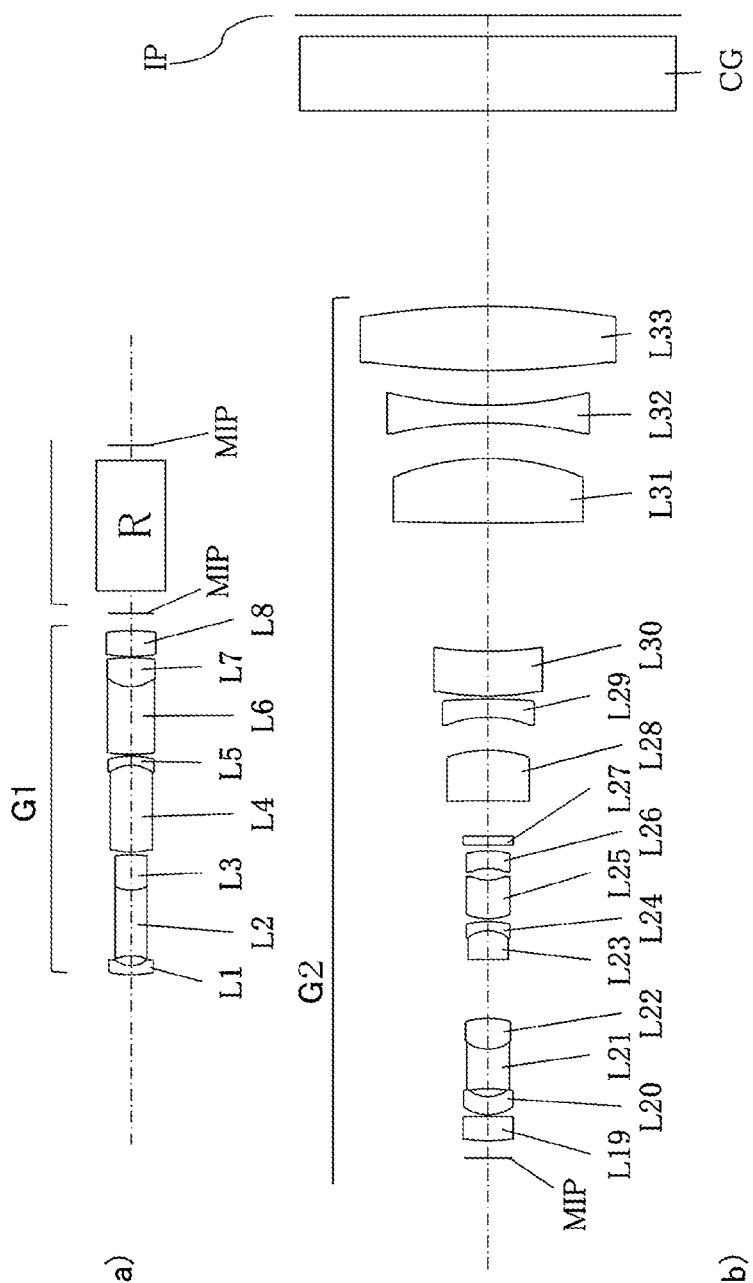
FIG. 3 is a lens sectional view of an observation optical system of example 2 according to the present invention at a time of focusing at infinity.

FIG. 3 shows a lens sectional view showing the lens configuration of an observation optical system according to example 2 of the present invention at a time of focusing at infinity. The observation optical system includes, from the observation object side: an objective lens system G1; and an image forming lens system G2 including a relay lens system R.

In the observation optical system, an intermediate object image is formed on a first intermediate image forming plane MIP through the objective lens system G1. In the image forming lens system G2, the intermediate object image is formed on a second intermediate image forming plane MIP through the relay lens system R, and then image-formed on an image plane IP of the image sensor. The image forming lens system G2 includes not only the relay lens system R but also a focus group that moves toward the object along the optical axis during focusing from an infinity object to a close object. FIG. 3(a) shows the objective lens system G1 and the relay lens system R in the upper part, and shows the lens configuration of the relay lens system R on the image plane side in the lower part.

The objective lens system G1 includes, from the observation object side: a negative meniscus lens L1 with the concave surface being oriented toward the image plane side; a cemented lens including a biconcave-shaped negative lens L2 and a biconvex-shaped positive lens L3 cemented to each other; an aperture regulation surface for defining the maximum aperture; a cemented lens including a biconvex-shaped positive lens L4 and a negative meniscus lens L5 with the concave surface being oriented toward the object side; a cemented lens including a negative meniscus lens L6 with the concave surface being oriented toward the image plane side and a biconvex-shaped positive lens L7 cemented to each other; and a biconvex-shaped positive lens L8.

The image forming lens system G2 includes, sequentially from the observation object side: a relay lens system R; a biconvex-shaped positive lens L19; a negative meniscus lens L20 with the concave surface being oriented toward the image plane side; a cemented lens including a biconcave-shaped negative lens L21 and a biconvex-shaped positive lens L22 cemented to each other; a cemented lens including a positive meniscus lens L23 with the convex surface being oriented toward the image plane side and a negative meniscus lens L24 with the concave surface being oriented toward the object side which are cemented to each other; a negative meniscus lens L25 with the concave surface being oriented toward the image plane side; a negative meniscus lens L26 with the concave surface being oriented toward the object side; a parallel plate L27; a positive meniscus lens L28 with the convex surface being oriented toward the image plane side; a negative meniscus lens L29 with the concave surface being oriented toward the object side; a positive meniscus lens L30 with the convex surface being oriented toward the image plane side; a biconvex-shaped positive lens L31; a biconcave-shaped negative lens L32; and a biconvex-shaped positive lens L33.

As shown in FIG. 3(b), the relay lens system R includes, sequentially from the observation object side: a biconvex-shaped positive lens L9; a cemented lens including a biconcave-shaped negative lens L10 and a biconvex-shaped positive lens L11 cemented to each other; a cemented lens including a biconcave-shaped negative lens L12 and a biconvex-shaped positive lens L13 cemented to each other; a cemented lens including a biconvex-shaped positive lens L14 and a biconcave-shaped negative lens L15 cemented to each other; a cemented lens including a biconvex-shaped positive lens L16 and a biconcave-shaped negative lens L17 cemented to each other; and a biconvex-shaped positive lens L18.

In the image forming lens system G2, the biconvex-shaped positive lens L31 is a focus group that moves toward the object side along the optical axis during focusing from an infinity object to a close object.

In this example, the image forming lens system G2 includes one relay lens system R. This example may have a configuration including multiple relay lens systems R. If the number of relay lens systems R included in the image forming lens system G2 is increased, the optical path length of the observation optical system can be increased. Consequently, the observation optical system suitable for interior observation of a narrow space that is long and thin can be obtained.

If the field curvature occurs owing to production error in this case, the occurring field curvature can be reduced by, for example, moving the relay lens system R in the optical axis direction.

If the one-side blurring occurs owing to production error, for example, the occurring one-side blurring can be reduced by integrally moving L32 and L33 included in the image forming lens system G2 in the direction perpendicular to the optical axis.

In this example, it is preferable that the pixel pitch P on the image plane IP of the image sensor range from 2 to 8 µm. The observation optical system of this example is also applicable to image sensors with pitches out of this range.

(2) Numerical Value Example

Figure 4:
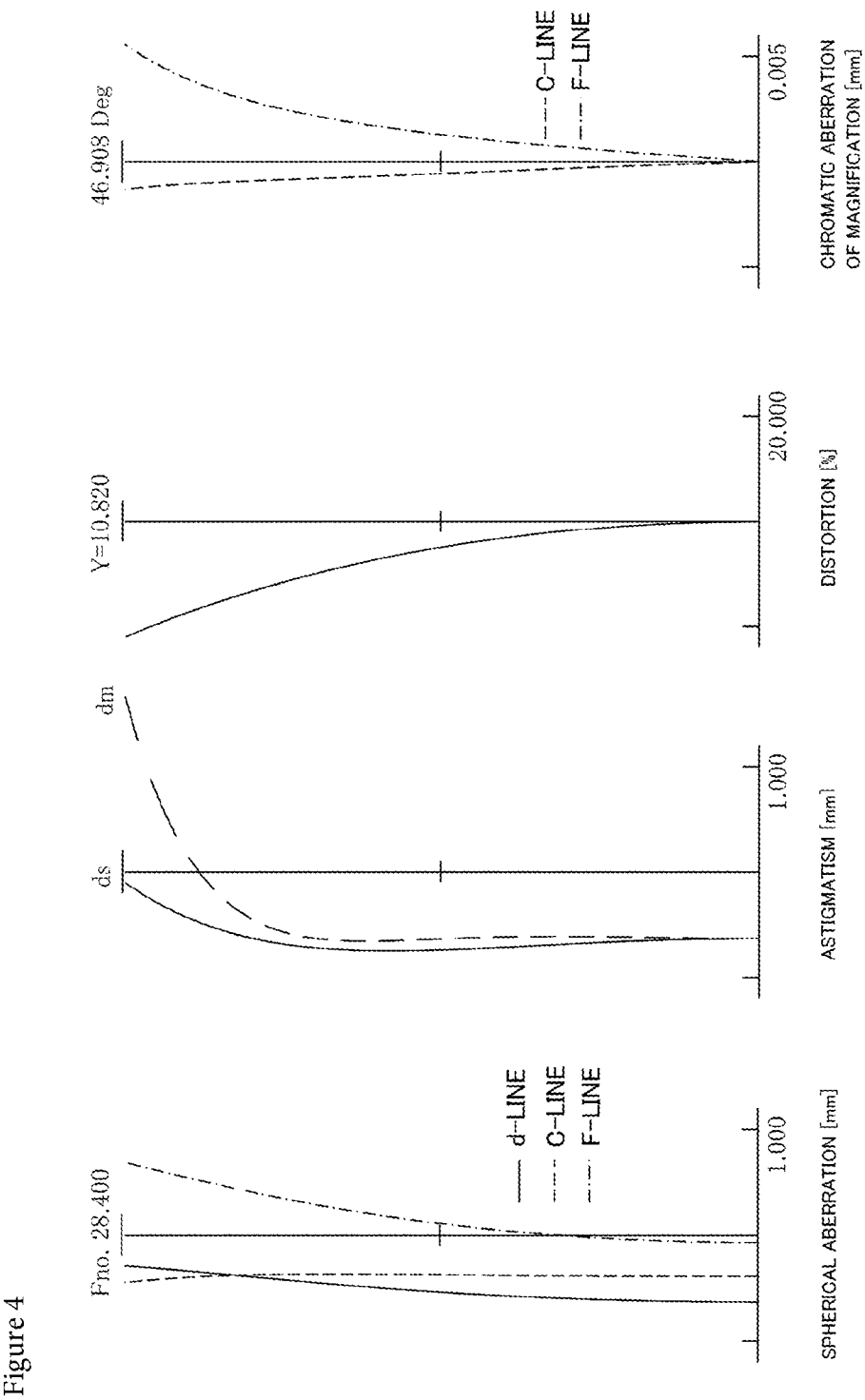
FIG. 4 is a spherical aberration diagram, an astigmatism diagram, a distortion aberration diagram, and a chromatic aberration of magnification diagram of the observation optical system according to example 2 at a time of focusing at infinity.

Next, numerical value examples where specific numerical values of the observation optical system are applied are described. Lens data on the observation optical system of this example is shown in Tables 4 and 5. Table 6 shows variable intervals on the optical axis, a specification table, and the focal length of each lens group, in the observation optical system. Furthermore, the numerical values of conditional expressions (1) to (9) are shown in Table 18. Furthermore, FIG. 4 shows longitudinal aberration diagrams of the optical system at a time of focusing at infinity.

TABLE 4

| Surface number | r | d | n | ν | Effective diameter |
|---|---|---|---|---|---|
| Object surface | ∞ | d0 | | | |
| 1 | ∞ | 0.0000 | | | 1.39 |
| 2 | ∞ | 0.0000 | | | 1.39 |
| 3 | 6.2000 | 0.5000 | 1.8830 | 40.81 | 1.26 |
| 4 | 1.3500 | 0.5333 | | | 0.87 |
| 5 | −2.2000 | 3.7150 | 1.8042 | 46.50 | 0.85 |
| 6 | 2.2000 | 1.9700 | 1.8467 | 23.78 | 0.89 |
| 7 S | −6.8500 | 0.1500 | | | 0.88 |
| 8 | 3.5050 | 4.9150 | 1.5688 | 56.04 | 0.92 |
| 9 | −1.9300 | 0.5000 | 1.8467 | 23.78 | 1.18 |
| 10 | −4.6800 | 0.0851 | | | 1.30 |
| 11 | 9.6000 | 3.8100 | 1.8467 | 23.78 | 1.32 |
| 12 | 2.0000 | 1.6550 | 1.4970 | 81.61 | 1.18 |
| 13 | −13.0000 | 0.1053 | | | 1.34 |
| 14 | 8.7000 | 1.4300 | 1.8467 | 23.78 | 1.38 |
| 15 | −10.8750 | 1.0002 | | | 1.39 |
| 16 | ∞ | 0.0000 | | | 1.31 |
| 17 | ∞ | 1.0038 | | | 1.31 |
| 18 | 9.4150 | 5.0000 | 1.9229 | 20.88 | 1.45 |
| 19 | −9.4150 | 0.1000 | | | 1.37 |
| 20 | −12.8000 | 7.2600 | 1.9037 | 31.32 | 1.35 |
| 21 | 2.9380 | 1.5950 | 1.8042 | 46.50 | 1.12 |
| 22 | −4.7700 | 0.3861 | | | 1.12 |
| 23 | −3.3150 | 0.5100 | 1.6989 | 30.05 | 1.04 |
| 24 | 2.9380 | 1.6300 | 1.7440 | 44.90 | 1.12 |
| 25 | −5.4000 | 0.1000 | | | 1.25 |
| 26 | ∞ | 0.0000 | | | 1.25 |
| 27 | ∞ | 0.1000 | | | 1.25 |
| 28 | 5.4000 | 1.6300 | 1.7440 | 44.90 | 1.25 |
| 29 | −2.9380 | 0.5100 | 1.6989 | 30.05 | 1.15 |
| 30 | 3.3150 | 0.3861 | | | 1.08 |
| 31 | 4.7700 | 1.5950 | 1.8042 | 46.50 | 1.13 |
| 32 | −2.9380 | 7.2600 | 1.9037 | 31.32 | 1.11 |
| 33 | 12.8000 | 0.1000 | | | 1.38 |
| 34 | 9.4150 | 5.0000 | 1.9229 | 20.88 | 1.40 |
| 35 | −9.4150 | 1.0038 | | | 1.46 |

TABLE 5

| Surface number | r | d | n | ν | Effective diameter |
|---|---|---|---|---|---|
| Object surface | ∞ | d0 | | | |
| 36 | ∞ | 0.0000 | | | 1.32 |
| 37 | ∞ | 1.0000 | | | 1.32 |
| 38 | 9.5650 | 1.3450 | 1.8061 | 33.27 | 1.40 |
| 39 | −65.3500 | 0.1000 | | | 1.40 |
| 40 | 2.2950 | 1.0250 | 1.9229 | 20.88 | 1.38 |
| 41 | 1.7500 | 0.4454 | | | 1.06 |
| 42 | −8.4175 | 2.2150 | 1.8467 | 23.78 | 1.06 |
| 43 | 2.0000 | 1.7400 | 1.8042 | 46.50 | 1.19 |
| 44 | −4.3150 | 3.3105 | | | 1.26 |
| 45 | −29.5500 | 1.6300 | 1.8052 | 25.46 | 1.00 |
| 46 | −1.7650 | 0.5100 | 1.8340 | 37.35 | 1.13 |
| 47 | −4.8050 | 0.1500 | | | 1.22 |
| 48 | 3.5650 | 2.1800 | 1.9229 | 20.88 | 1.22 |
| 49 | 2.0000 | 0.6606 | | | 0.87 |
| 50 | −2.2400 | 1.0000 | 1.4970 | 81.61 | 0.93 |

TABLE 5-continued

| Surface number | r | d | n | v | Effective diameter |
|---|---|---|---|---|---|
| 51 | −3.6850 | 0.3000 | | | 1.22 |
| 52 | ∞ | 0.5000 | 1.9108 | 35.25 | 1.35 |
| 53 | ∞ | 1.0000 | | | 1.42 |
| 54 | ∞ | 0.0000 | | | 1.68 |
| 55 | ∞ | 1.0000 | | | 1.68 |
| 56 | −53.4195 | 2.8235 | 1.9108 | 35.25 | 1.94 |
| 57 | −7.7839 | 1.8792 | | | 2.32 |
| 58 | −6.4734 | 1.0000 | 1.9212 | 23.96 | 2.32 |
| 59 | −30.6031 | 0.2000 | | | 2.57 |
| 60 | 15.3070 | 2.5397 | 1.4970 | 81.61 | 2.73 |
| 61 | 22.3718 | d61 | | | 3.04 |
| 62 | 176.9876 | 3.6391 | 1.5168 | 64.20 | 4.91 |
| 63 | −13.8504 | d63 | | | 5.32 |
| 64 | −24.0675 | 1.0000 | 1.8810 | 40.14 | 5.39 |
| 65 | 22.5600 | 1.9370 | | | 5.68 |
| 66 | 45.7898 | 3.5777 | 1.8081 | 22.76 | 6.67 |
| 67 | −44.4021 | 11.0000 | | | 7.18 |
| 68 | ∞ | 4.2000 | 1.5168 | 64.20 | 9.90 |
| 69 | ∞ | 1.0000 | | | 10.57 |
| 70 | ∞ | 0.0000 | | | 10.88 |

TABLE 6

[Variable interval]

| d0 | ∞ | 100.0000 | 50.0000 | 25.0000 | 10.0000 |
|---|---|---|---|---|---|
| d61 | 7.2038 | 6.5702 | 5.9782 | 4.8961 | 2.1803 |
| d63 | 2.0000 | 2.6336 | 3.2256 | 4.3077 | 7.0234 |

[Specification table]

| F | 12.209 |
|---|---|
| Fno. | 28.636 |
| Optical overall length | 119.850 |
| ω | 46.9080 |
| Y | 10.8200 |

[Focal length of each lens system/group]

| | Surface number | Focal length |
|---|---|---|
| Objective lens system | 3-16 | 1.575 |
| Relay lens system | 17-36 | −104.059 |
| Front side lens group | 37-61 | 4.880 |
| Focus group | 62-63 | 24.926 |
| Rear side lens group | 64-67 | −30.745 |
| Image forming lens system | 17-67 | −5.794 |

Example 3

(1) Configuration of Observation Optical System

Figure 5:
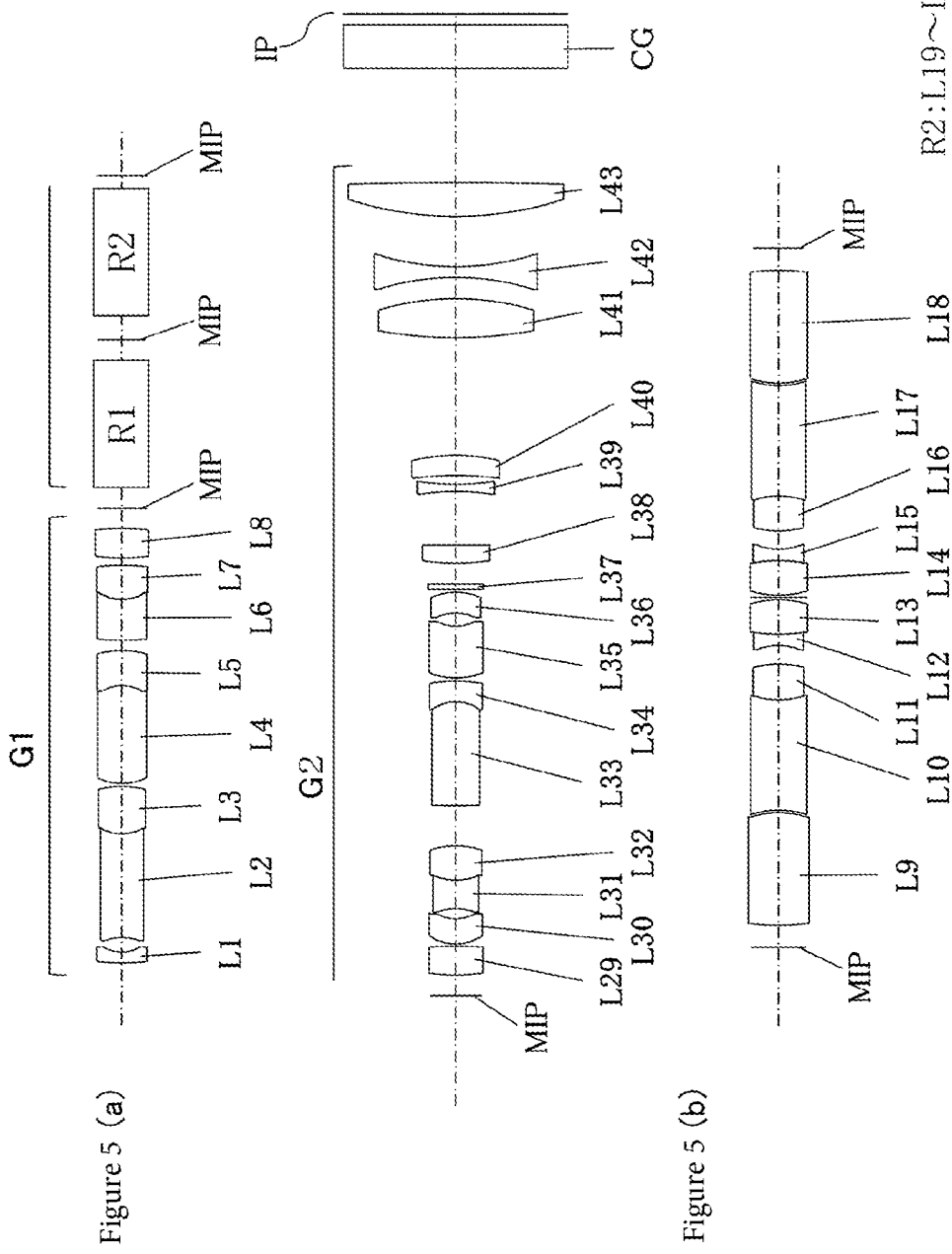
FIG. 5 is a lens sectional view of an observation optical system of example 3 according to the present invention at a time of focusing at infinity.

FIG. 5 shows a lens sectional view showing the lens configuration of an observation optical system according to example 3 of the present invention at a time of focusing at infinity. The observation optical system includes, from the observation object side: an objective lens system G1; and an image forming lens system G2 that includes a first relay lens system R1 and a second relay lens system R2. In the observation optical system, an intermediate object image is formed on a first intermediate image forming plane MIP through the objective lens system G1. In the image forming lens system G2, the intermediate object image is formed on a second intermediate image forming plane MIP through the first relay lens system R1 and formed on a third intermediate image forming plane MIP through the second relay lens system R2, and then image-formed on an image plane IP of the image sensor. The image forming lens system G2 includes not only the first relay lens system R1 and the second relay lens system R2 but also a focus group that moves toward the object side along the optical axis during focusing from an infinity object to a close object. Note that FIG. 5(a) shows the objective lens system G1, the first relay lens system R1 and the second relay lens system R2 in the upper part, and shows the lens configuration of the second relay lens system R2 on the image plane side in the lower part. Furthermore, FIG. 5(b) shows the configuration of the first relay lens system R1. The lens configuration of the second relay lens system R2 is substantially identical to that of the first relay lens system R1, and includes lenses L19 to L28, not shown.

The objective lens system G1 includes, from the observation object side: a negative meniscus lens L1 with the concave surface being oriented toward the image plane side; a cemented lens including a biconcave-shaped negative lens L2 and a biconvex-shaped positive lens L3 cemented to each other; an aperture regulation surface for defining the maximum aperture; a cemented lens including a biconvex-shaped positive lens L4 and a negative meniscus lens L5 with the concave surface being oriented toward the object side; a cemented lens including a negative meniscus lens L6 with the concave surface being oriented toward the image plane side and a biconvex-shaped positive lens L7 cemented to each other; and a biconvex-shaped positive lens L8.

The image forming lens system G2 includes, sequentially from the observation object side: a first relay lens system R1; a second a relay lens system R2; a biconvex-shaped positive lens L29; a negative meniscus lens L30 with the concave surface being oriented toward the image plane side; a cemented lens including a biconcave-shaped negative lens L31 and a biconvex-shaped positive lens L32 cemented to each other; a cemented lens including a positive meniscus lens L33 with the convex surface being oriented toward the image plane side and a negative meniscus lens L34 with the concave surface being oriented toward the object side which are cemented to each other; a negative meniscus lens L35 with the concave surface being oriented toward the image plane side; a negative meniscus lens L36 with the concave surface being oriented toward the object side; a parallel plate L37; a positive lens L38 with the convex surface being oriented toward the object side; a biconcave-shaped negative lens L39; a positive meniscus lens L40 with the convex surface being oriented toward the image plane side; a biconvex-shaped positive lens L41; a biconcave-shaped negative lens L42; and a biconvex-shaped positive lens L43.

As shown in FIG. 5(b), the first relay lens system R1 includes, sequentially from the observation object side: a biconvex-shaped positive lens L9; a cemented lens including a biconcave-shaped negative lens L10 and a biconvex-shaped positive lens L11 cemented to each other; a cemented lens including a biconcave-shaped negative lens L12 and a biconvex-shaped positive lens L13 cemented to each other; a cemented lens including a biconvex-shaped positive lens L14 and a biconcave-shaped negative lens L15 cemented to each other; a cemented lens including a biconvex-shaped positive lens L16 and a biconcave-shaped negative lens L17 cemented to each other; and a biconvex-shaped positive lens L18.

Although illustration is omitted, the second relay lens system R2 has a lens configuration analogous to that of the first relay lens system R1, and includes, sequentially from the observation object side: a biconvex-shaped positive lens L19; a cemented lens including a biconcave-shaped negative lens L20 and a biconvex-shaped positive lens L21 cemented to each other; a cemented lens including a biconcave-shaped negative lens L22 and a biconvex-shaped positive lens L23 cemented to each other; a cemented lens including a biconvex-shaped positive lens L24 and a biconcave-shaped negative lens L25 cemented to each other; a cemented lens including a biconvex-shaped positive lens L26 and a biconcave-shaped negative lens L27 cemented to each other; and a biconvex-shaped positive lens L28.

In the image forming lens system G2, the biconvex-shaped positive lens L41 is a focus group that moves toward the object side along the optical axis during focusing from an infinity object to a close object.

In this example, the image forming lens system G2 includes the first relay lens system R1 and the second relay lens system R2. This example includes two relay lens systems. If the number of relay lens systems included in the image forming lens system G2 is further increased, the optical path length of the observation optical system can be further increased. Consequently, the observation optical system suitable for interior observation of a narrow space that is long and thin can be obtained. If the number of relay lens systems is reduced, an observation optical system having a higher image forming performance can be achieved.

If the field curvature occurs owing to production error in this case, the occurring field curvature can be reduced by, for example, moving the first relay lens system R1 in the optical axis direction.

If the one-side blurring occurs owing to production error, for example, the occurring one-side blurring can be reduced by integrally moving L42 and L43 included in the image forming lens system G2 in the direction perpendicular to the optical axis.

In this example, it is preferable that the pixel pitch P on the image plane IP of the image sensor range from 2 to 8 μm.

The observation optical system of this example is also applicable to image sensors with pitches out of this range.

(2) Numerical Value Example

Figure 6:
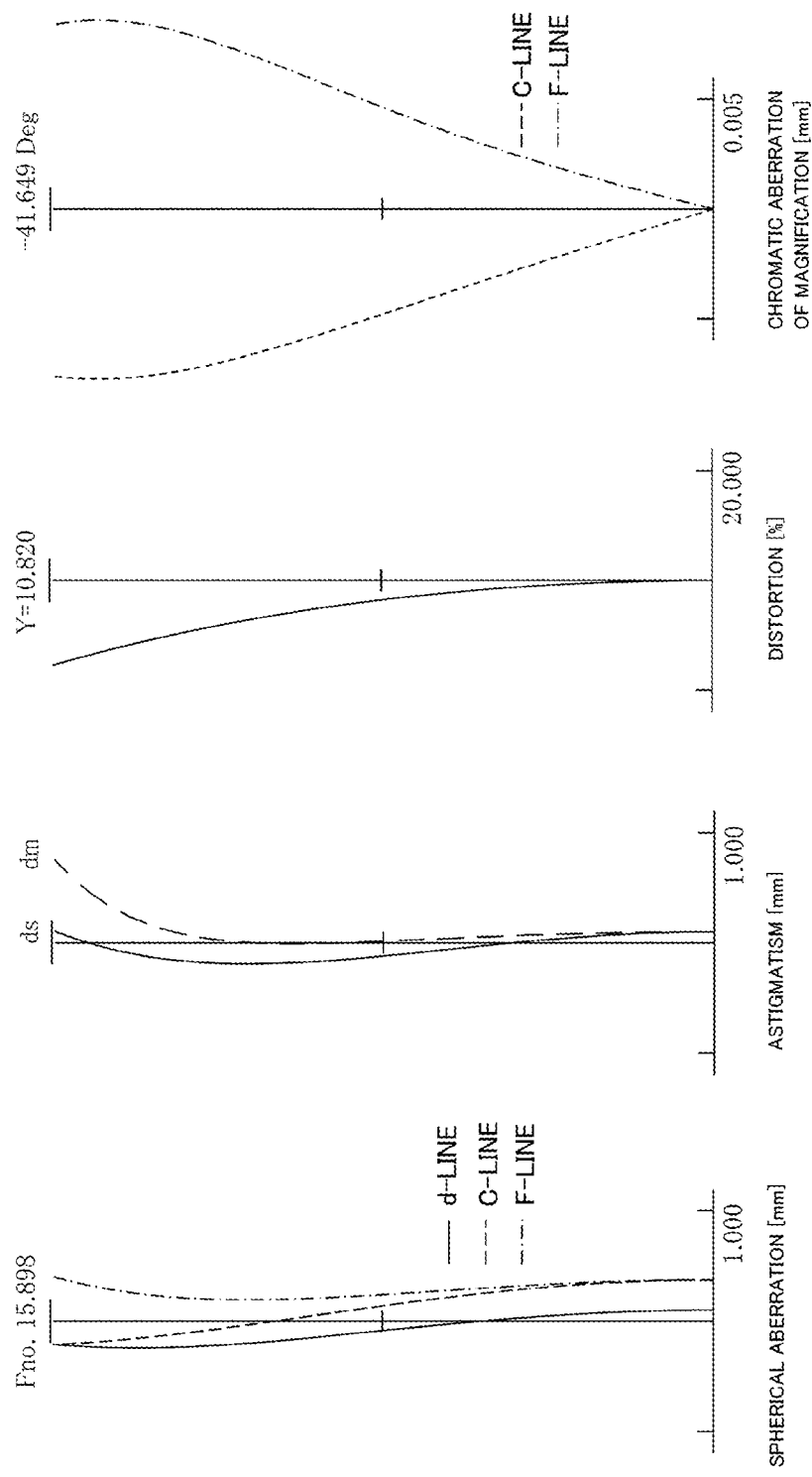
FIG. 6 is a spherical aberration diagram, an astigmatism diagram, a distortion aberration diagram, and a chromatic aberration of magnification diagram of the observation optical system according to example 3 at a time of focusing at infinity.

Next, numerical value examples where specific numerical values of the observation optical system are applied are described. Lens data on the observation optical system of this example is shown in Tables 7 to 9. Table 10 shows variable intervals on the optical axis, a specification table, and the focal length of each lens group, in the observation optical system. Furthermore, the numerical values of conditional expressions (1) to (9) are shown in Table 18. Furthermore, FIG. 6 shows longitudinal aberration diagrams of the optical system at a time of focusing at infinity.

TABLE 7

| Surface number | | r | d | n | ν | Effective diameter |
|---|---|---|---|---|---|---|
| Object surface | | ∞ | d0 | | | |
| 1 | | ∞ | 0.0000 | | | 2.53 |
| 2 | | ∞ | 0.0000 | | | 2.53 |
| 3 | | 23.6254 | 1.0000 | 1.8467 | 23.78 | 2.42 |
| 4 | | 3.1003 | 1.4112 | | | 1.77 |
| 5 | | −4.5722 | 10.0000 | 1.8830 | 40.81 | 1.62 |
| 6 | | 4.0176 | 0.0100 | 1.5673 | 42.70 | 2.07 |
| 7 | | 4.0176 | 4.5471 | 1.8467 | 23.78 | 2.07 |
| 8 | S | −10.1471 | 0.3000 | | | 2.27 |
| 9 | | 5.4331 | 9.4351 | 1.4970 | 81.61 | 2.33 |
| 10 | | −3.5001 | 0.0100 | 1.5673 | 42.70 | 1.94 |
| 11 | | −3.5001 | 3.3373 | 2.0007 | 25.46 | 1.94 |
| 12 | | −9.0978 | 1.0243 | | | 2.40 |
| 13 | | 35.1454 | 3.9081 | 1.8467 | 23.78 | 2.38 |
| 14 | | 4.0244 | 0.0100 | 1.5673 | 42.70 | 2.20 |
| 15 | | 4.0244 | 3.2875 | 1.4970 | 81.61 | 2.20 |
| 16 | | −23.7698 | 0.7116 | | | 2.46 |
| 17 | | 20.8583 | 2.7965 | 2.0010 | 29.13 | 2.56 |

TABLE 7-continued

| Surface number | r | d | n | ν | Effective diameter |
|---|---|---|---|---|---|
| 18 | −25.0241 | 2.0000 | | | 2.53 |
| 19 | ∞ | 0.0000 | | | 2.46 |
| 20 | ∞ | 2.0000 | | | 2.46 |
| 21 | 17.6965 | 10.0000 | 1.8467 | 23.78 | 2.70 |
| 22 | −8.4619 | 0.2542 | | | 2.54 |
| 23 | −7.1590 | 9.7886 | 1.6889 | 31.16 | 2.47 |
| 24 | 6.8408 | 0.0100 | 1.5673 | 42.70 | 2.26 |
| 25 | 6.8408 | 3.1727 | 1.6385 | 55.45 | 2.26 |
| 26 | −8.8959 | 1.6484 | | | 2.27 |
| 27 | −5.2194 | 1.0000 | 1.7282 | 28.32 | 2.00 |
| 28 | 12.3569 | 0.0100 | 1.5673 | 42.70 | 2.19 |
| 29 | 12.3569 | 3.0695 | 1.8348 | 42.72 | 2.19 |
| 30 | −8.4553 | 0.2000 | | | 2.54 |
| 31 | ∞ | 0.0000 | | | 2.54 |
| 32 | ∞ | 0.2000 | | | 2.54 |
| 33 | 8.4553 | 3.0695 | 1.8348 | 42.72 | 2.54 |
| 34 | −12.3569 | 0.0100 | 1.5673 | 42.70 | 2.25 |
| 35 | −12.3569 | 1.0000 | 1.7282 | 28.32 | 2.25 |
| 36 | 5.2194 | 1.6484 | | | 2.05 |
| 37 | 8.8959 | 3.1727 | 1.6385 | 55.45 | 2.22 |
| 38 | −6.8408 | 0.0100 | 1.5673 | 42.70 | 2.22 |
| 39 | −6.8408 | 9.7886 | 1.6889 | 31.16 | 2.22 |
| 40 | 7.1590 | 0.2542 | | | 2.39 |

TABLE 8

| Surface number | r | d | n | ν | Effective diameter |
|---|---|---|---|---|---|
| Object surface | ∞ | d0 | | | |
| 41 | 8.4619 | 10.0000 | 1.8467 | 23.78 | 2.46 |
| 42 | −17.6965 | 2.0000 | | | 2.53 |
| 43 | ∞ | 0.0000 | | | 2.28 |
| 44 | ∞ | 2.0000 | | | 2.28 |
| 45 | 17.6965 | 10.0000 | 1.8467 | 23.78 | 2.52 |
| 46 | −8.4619 | 0.2542 | | | 2.54 |
| 47 | −7.1590 | 9.7886 | 1.6889 | 31.16 | 2.48 |
| 48 | 6.8408 | 0.0100 | 1.5673 | 42.70 | 2.50 |
| 49 | 6.8408 | 3.1727 | 1.6385 | 55.45 | 2.50 |
| 50 | −8.8959 | 1.6484 | | | 2.53 |
| 51 | −5.2194 | 1.0000 | 1.7282 | 28.32 | 2.26 |
| 52 | 12.3569 | 0.0100 | 1.5673 | 42.70 | 2.45 |
| 53 | 12.3569 | 3.0695 | 1.8348 | 42.72 | 2.45 |
| 54 | −8.4553 | 0.2000 | | | 2.65 |
| 55 | ∞ | 0.0000 | | | 2.58 |
| 56 | ∞ | 0.2000 | | | 2.58 |
| 57 | 8.4553 | 3.0695 | 1.8348 | 42.72 | 2.55 |
| 58 | −12.3569 | 0.0100 | 1.5673 | 42.70 | 2.19 |
| 59 | −12.3569 | 1.0000 | 1.7282 | 28.32 | 2.19 |
| 60 | 5.2194 | 1.6484 | | | 1.98 |
| 61 | 8.8959 | 3.1727 | 1.6385 | 55.45 | 2.21 |
| 62 | −6.8408 | 0.0100 | 1.5673 | 42.70 | 2.23 |
| 63 | −6.8408 | 9.7886 | 1.6889 | 31.16 | 2.23 |
| 64 | 7.1590 | 0.2542 | | | 2.50 |
| 65 | 8.4619 | 10.0000 | 1.8467 | 23.78 | 2.57 |
| 66 | −17.6965 | 2.0000 | | | 2.71 |
| 67 | ∞ | 0.0000 | | | 2.46 |
| 68 | ∞ | 2.0000 | | | 2.46 |
| 69 | 18.9703 | 2.7535 | 1.8830 | 40.81 | 2.56 |
| 70 | −37.3793 | 0.2000 | | | 2.59 |
| 71 | 4.5455 | 2.4358 | 2.0010 | 29.13 | 2.56 |
| 72 | 3.5004 | 0.9758 | | | 1.83 |
| 73 | −5.3205 | 2.7479 | 1.8467 | 23.78 | 1.82 |
| 74 | 5.8756 | 0.0100 | 1.5673 | 42.70 | 2.22 |
| 75 | 5.8756 | 3.2605 | 1.8348 | 42.72 | 2.22 |
| 76 | −7.8752 | 3.8788 | | | 2.50 |
| 77 | 36.4329 | 10.0000 | 1.9229 | 20.88 | 2.23 |
| 78 | −3.8888 | 0.0100 | 1.5673 | 42.70 | 2.29 |
| 79 | −3.8888 | 2.0000 | 2.0007 | 25.46 | 2.29 |
| 80 | −14.6247 | 0.3000 | | | 2.53 |

TABLE 9

| Surface number | r | d | n | ν | Effective diameter |
|---|---|---|---|---|---|
| Object surface | ∞ | d0 | | | |
| 81 | 6.8646 | 4.9960 | 1.8467 | 23.78 | 2.57 |
| 82 | 3.8096 | 1.2327 | | | 1.77 |
| 83 | −4.5179 | 2.0000 | 1.4970 | 81.61 | 1.86 |
| 84 | −6.3240 | 0.3000 | | | 2.41 |
| 85 | ∞ | 0.5000 | 1.9037 | 31.32 | 2.59 |
| 86 | ∞ | 1.0000 | | | 2.65 |
| 87 | ∞ | 0.0000 | | | 2.88 |
| 88 | ∞ | 1.0000 | | | 2.88 |
| 89 | 19.5400 | 1.7700 | 1.8830 | 40.81 | 3.17 |
| 90 | ∞ | 5.1949 | | | 3.23 |
| 91 | −24.7300 | 0.7000 | 1.8052 | 25.46 | 3.57 |
| 92 | 24.7300 | 0.8667 | | | 3.70 |
| 93 | −27.7000 | 1.9200 | 1.8042 | 46.50 | 3.82 |
| 94 | −16.8350 | d94 | | | 4.23 |
| 95 | 42.3300 | 3.7300 | 1.4970 | 81.61 | 7.26 |
| 96 | −25.6100 | d96 | | | 7.46 |
| 97 | −24.4000 | 1.0000 | 1.6034 | 38.01 | 7.44 |
| 98 | 24.4000 | 4.8439 | | | 7.85 |
| 99 | 33.3000 | 3.2500 | 2.0007 | 25.46 | 10.32 |
| 100 | −385.4000 | 11.0000 | | | 10.36 |
| 101 | ∞ | 4.2000 | 1.5168 | 64.20 | 10.68 |
| 102 | ∞ | 1.0000 | | | 10.79 |
| 103 | ∞ | 0.0000 | | | 10.85 |

TABLE 10

[Variable interval]

| d0 | ∞ | 100.0000 | 50.0000 | 25.0000 | 10.0000 |
|---|---|---|---|---|---|
| d94 | 11.3409 | 10.1139 | 9.0193 | 7.1269 | 2.8161 |
| d96 | 2.0654 | 3.2924 | 4.3870 | 6.2794 | 10.5902 |

[Specification table]

| f | −14.0705 |
|---|---|
| Fno. | 15.9829 |
| Optical overall length | 262.8854 |
| ω | 41.6490 |
| Y | 10.8200 |

[Focal length of each lens system/group]

| | Surface number | Focal length |
|---|---|---|
| Objective lens system | 3-19 | 3.209 |
| Relay lens system | 21-67 | −83.528 |
| Front side lens group | 68-94 | 9.883 |
| Focus group | 95-96 | 32.607 |
| Rear side lens group | 97-100 | −115.756 |
| Image forming lens system | 21-100 | 25.966 |

Example 4

(1) Configuration of Observation Optical System

Figure 7:
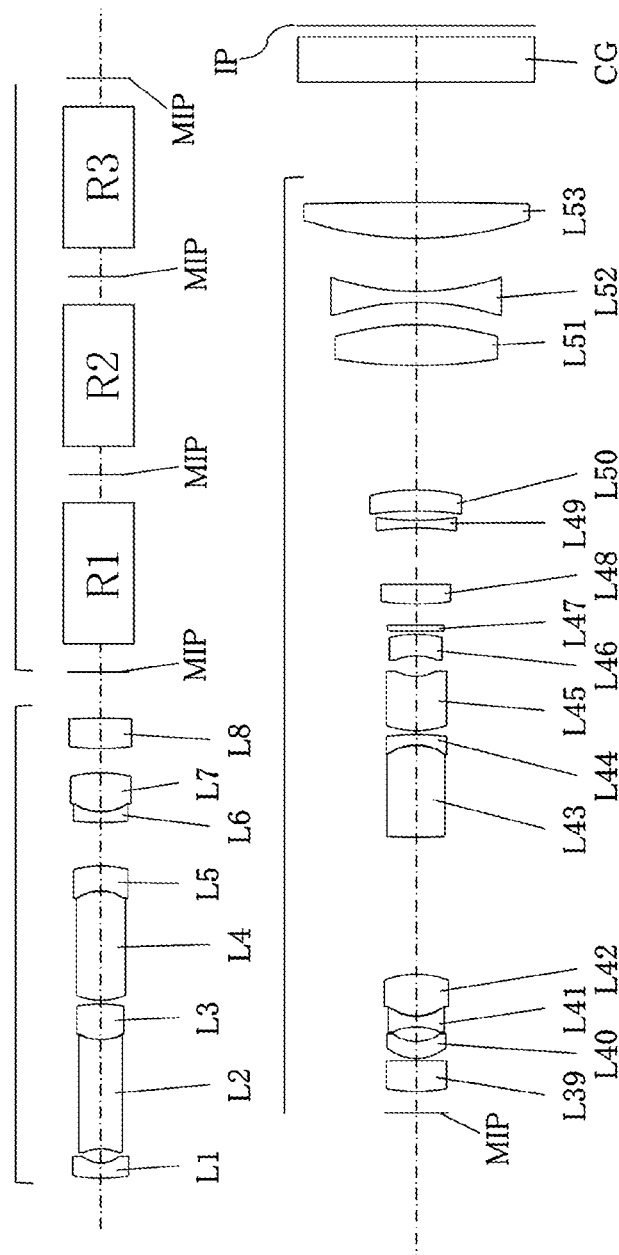
FIG. 7 is a lens sectional view of an observation optical system of example 4 according to the present invention at a time of focusing at infinity.
Figure 7:
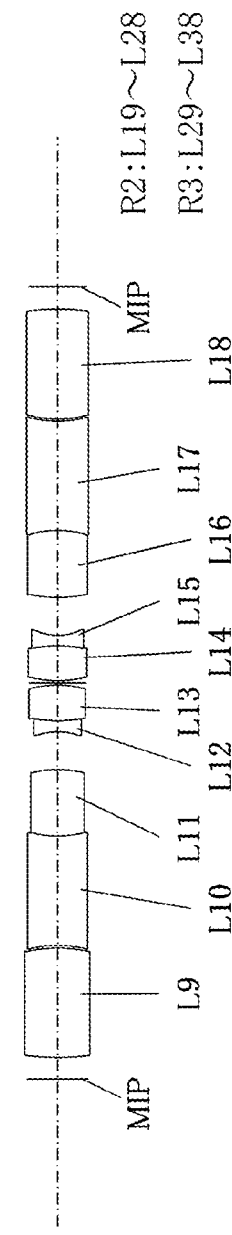

FIG. 7 shows a lens sectional view showing the lens configuration of the observation optical system according to example 4 of the present invention at a time of focusing at infinity. The observation optical system includes, from the observation object side: an objective lens system G1; and an image forming lens system G2 that includes a first relay lens system R1, a second relay lens system R2 and a third relay lens system R3. In the observation optical system, an intermediate object image is formed on a first intermediate image forming plane MIP through the objective lens system G1. In the image forming lens system G2, the intermediate object image is formed on a second intermediate image forming plane MIP through the first relay lens system R1, is formed on a third intermediate image forming plane MIP through the second relay lens system R2 and is formed on a fourth intermediate image forming plane MIP through the third relay lens system R3, and then is image-formed on an image plane IP of the image sensor. The image forming lens system G2 includes not only the first relay lens system R1, the second relay lens system R2 and the third relay lens system R3, but also a focus group that moves toward the object side along the optical axis during focusing from an infinity object to a close object. Note that FIG. 7(a) shows the objective lens system G1, the first relay lens system R1, the second relay lens system R2 and the third relay lens system R3 in the upper part, and shows the lens configuration of the third relay lens system R3 on the image plane side in the lower part. Furthermore, FIG. 7(b) shows the configuration of the first relay lens system R1. The lens configurations of the second relay lens system R2 and the third relay lens system R3 are substantially identical to the lens configuration of the first relay lens system R1, and includes lenses L19 to L28 and lenses L29 to 38, not shown.

The objective lens system G1 includes, from the observation object side: a negative meniscus lens L1 with the concave surface being oriented toward the image plane side; a cemented lens including a biconcave-shaped negative lens L2 and a biconvex-shaped positive lens L3 cemented to each other; an aperture regulation surface for defining the maximum aperture; a cemented lens including a biconvex-shaped positive lens L4 and a negative meniscus lens L5 with the concave surface being oriented toward the object; a cemented lens including a negative meniscus lens L6 with the concave surface being oriented toward the image plane and a biconvex-shaped positive lens L7 cemented to each other; and a biconvex-shaped positive lens L8.

The image forming lens system G2 includes, sequentially from the observation object side: a first relay lens system R1; a second a relay lens system R2; a third relay lens system R3; a biconvex-shaped positive lens L39; a negative meniscus lens L40 with the concave surface being oriented toward the image plane side; a cemented lens including a biconcave-shaped negative lens L41 and a biconvex-shaped positive lens L42 cemented to each other; a cemented lens including a positive meniscus lens L43 with the convex surface being oriented toward the image plane side and a negative meniscus lens L44 with the concave surface being oriented toward the object side which are cemented to each other; a negative meniscus lens L45 with the concave surface being oriented toward the image plane side; a negative meniscus lens L46 with the concave surface being oriented toward the object side; a parallel plate L47; a positive lens L48 with the convex surface being oriented toward the object side; a biconcave-shaped negative lens L49; a positive meniscus lens L50 with the convex surface being oriented toward the image plane side; a biconvex-shaped positive lens L51; a biconcave-shaped negative lens L52; and a biconvex-shaped positive lens L53.

As shown in FIG. 7(b), the first relay lens system R1 includes, sequentially from the observation object side: a biconvex-shaped positive lens L9; a cemented lens including a biconcave-shaped negative lens L10 and a biconvex-shaped positive lens L11 cemented to each other; a cemented lens including a biconcave-shaped negative lens L12 and a biconvex-shaped positive lens L13 cemented to each other; a cemented lens including a biconvex-shaped positive lens L14 and a biconcave-shaped negative lens L15 cemented to each other; a cemented lens including a biconvex-shaped positive lens L16 and a biconcave-shaped negative lens L17 cemented to each other; and a biconvex-shaped positive lens L18.

Although illustration is omitted, the second relay lens system R2 has a lens configuration analogous to that of the first relay lens system R1, and includes, sequentially from the observation object side: a biconvex-shaped positive lens L19; a cemented lens including a biconcave-shaped negative lens L20 and a biconvex-shaped positive lens L21 cemented to each other; a cemented lens including a biconcave-shaped negative lens L22 and a biconvex-shaped positive lens L23 cemented to each other; a cemented lens including a biconvex-shaped positive lens L24 and a biconcave-shaped negative lens L25 cemented to each other; a cemented lens including a biconvex-shaped positive lens L26 and a biconcave-shaped negative lens L27 cemented to each other; and a biconvex-shaped positive lens L28.

Although illustration is also omitted, the third relay lens system R3 has a lens configuration analogous to that of the first relay lens system R1, and includes, sequentially from the observation object side: a biconvex-shaped positive lens L29; a cemented lens including a biconcave-shaped negative lens L30 and a biconvex-shaped positive lens L31 cemented to each other; a cemented lens including a biconcave-shaped negative lens L32 and a biconvex-shaped positive lens L33 cemented to each other; a cemented lens including a biconvex-shaped positive lens L34 and a biconcave-shaped negative lens L35 cemented to each other; a cemented lens including a biconvex-shaped positive lens L36 and a biconcave-shaped negative lens L37 cemented to each other; and a biconvex-shaped positive lens L38.

In the image forming lens system G2, the biconvex-shaped positive lens L51 is a focus group that moves toward the object side along the optical axis during focusing from an infinity object to a close object.

In this example, the image forming lens system G2 includes the first relay lens system R1, the second relay lens system R2 and the third relay lens system R3. This example includes three relay lens systems. If the number of relay lens systems included in the image forming lens system G2 is further increased, the optical path length of the observation optical system can be further increased. Consequently, the observation optical system suitable for interior observation of a narrow space that is further long and thin can be obtained. If the number of relay lens systems is reduced, an observation optical system having a higher image forming performance can be achieved.

If the field curvature occurs owing to production error in this case, the occurring field curvature can be reduced by, for example, moving the first relay lens system R1 in the optical axis direction.

If the one-side blurring occurs owing to production error, for example, the occurring one-side blurring can be reduced by integrally moving L52 and L53 included in the image forming lens system G2 in the direction perpendicular to the optical axis.

In this example, it is preferable that the pixel pitch P on the image plane IP of the image sensor range from 2 to 8 μm. The observation optical system of this example is also applicable to image sensors with pitches out of this range.

(2) Numerical Value Example

Figure 8:
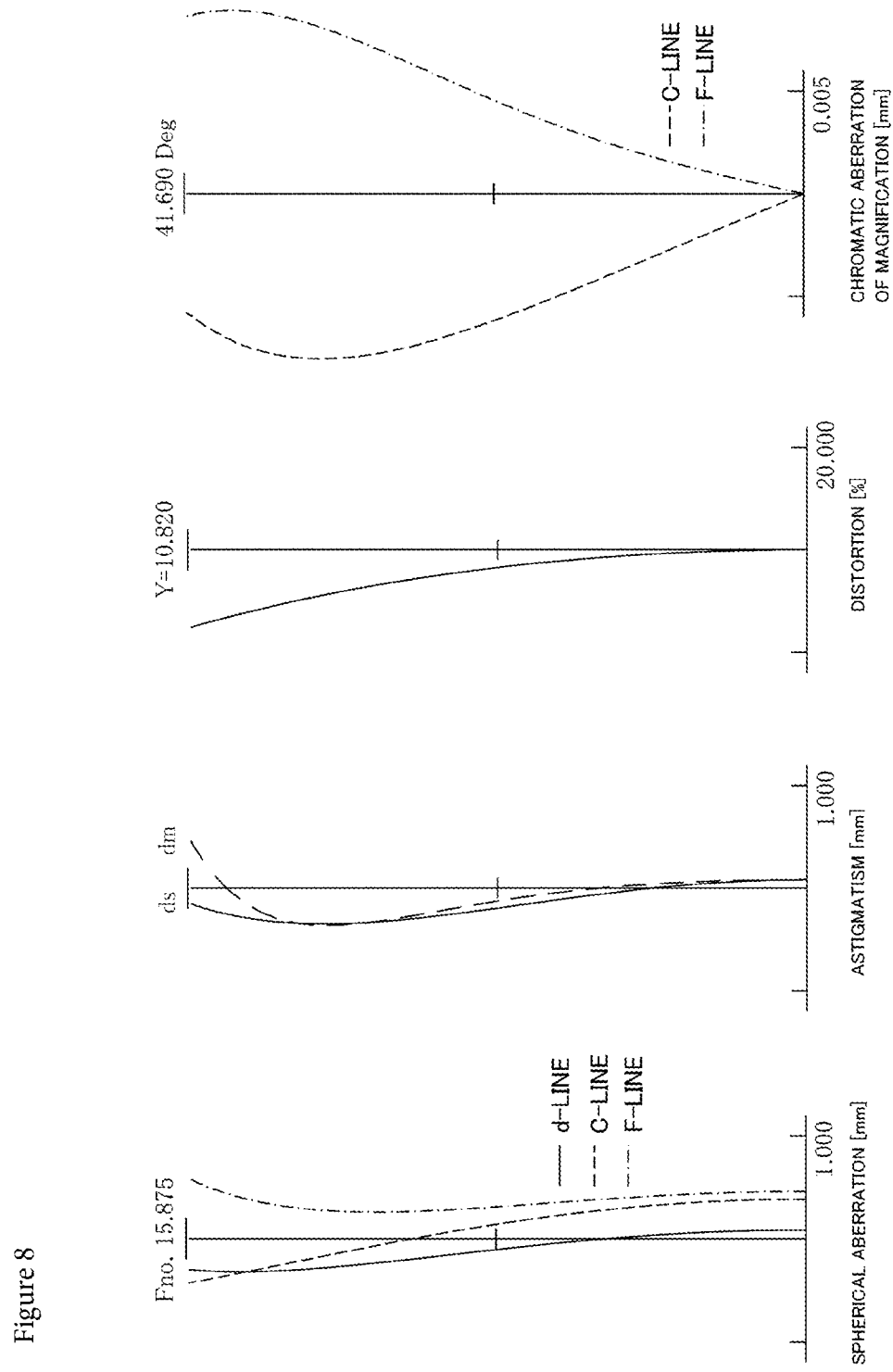
FIG. 8 is a spherical aberration diagram, an astigmatism diagram, a distortion aberration diagram, and a chromatic aberration of magnification diagram of the observation optical system according to example 4 at a time of focusing at infinity.

Next, numerical value examples where specific numerical values of the observation optical system are applied are described. Lens data on the observation optical system of this example is shown in Tables 11, 12 and 13. Table 14 shows variable intervals on the optical axis, a specification table, and the focal length of each lens group, in the observation optical system. Furthermore, the numerical values of conditional expressions (1) to (9) are shown in Table 18. Furthermore, FIG. 8 shows longitudinal aberration diagrams of the optical system at a time of focusing at infinity.

TABLE 11

| Surface number | | r | d | n | ν | Effective diameter |
|---|---|---|---|---|---|---|
| Object surface | | ∞ | d0 | | | |
| 1 | | ∞ | 0.0000 | | | 2.83 |
| 2 | | ∞ | 0.0000 | | | 2.83 |
| 3 | | 11.3791 | 1.4379 | 1.8467 | 23.78 | 2.57 |
| 4 | | 2.7302 | 1.2499 | | | 1.65 |
| 5 | | −3.6439 | 10.0000 | 1.8830 | 40.81 | 1.52 |
| 6 | | 4.5466 | 0.0100 | 1.5673 | 42.70 | 2.00 |
| 7 | | 4.5466 | 3.2784 | 1.8467 | 23.78 | 2.01 |
| 8 | S | −10.0000 | 0.3000 | | | 2.15 |
| 9 | | 5.6462 | 10.0000 | 1.4970 | 81.61 | 2.22 |
| 10 | | −3.6233 | 0.0100 | 1.5673 | 42.70 | 2.08 |
| 11 | | −3.6233 | 2.3003 | 2.0007 | 25.46 | 2.08 |
| 12 | | −8.4850 | 3.9295 | | | 2.48 |
| 13 | | 27.1355 | 1.0000 | 1.8467 | 23.78 | 2.52 |
| 14 | | 4.4598 | 0.0100 | 1.5673 | 42.70 | 2.45 |
| 15 | | 4.4598 | 3.5752 | 1.4970 | 81.61 | 2.46 |
| 16 | | −11.7819 | 2.2384 | | | 2.73 |
| 17 | | 24.6771 | 2.7548 | 2.0010 | 29.13 | 2.85 |
| 18 | | −49.8863 | 2.0000 | | | 2.76 |
| 19 | | ∞ | 0.0000 | | | 2.82 |
| 20 | | ∞ | 2.0000 | | | 2.82 |
| 21 | | 24.9786 | 10.0000 | 1.8467 | 23.78 | 2.98 |
| 22 | | −11.0902 | 0.2212 | | | 2.80 |
| 23 | | −10.0707 | 10.0000 | 1.7174 | 29.50 | 2.75 |
| 24 | | 9.4890 | 0.0100 | 1.5673 | 42.70 | 2.41 |
| 25 | | 9.4890 | 6.0938 | 1.7170 | 47.98 | 2.41 |
| 26 | | −11.5448 | 3.4592 | | | 2.31 |
| 27 | | −5.4450 | 1.0000 | 1.7282 | 28.32 | 1.94 |
| 28 | | 12.2237 | 0.0100 | 1.5673 | 42.70 | 2.17 |
| 29 | | 12.2237 | 3.2435 | 1.8348 | 42.72 | 2.17 |
| 30 | | −9.0028 | 0.2000 | | | 2.59 |
| 31 | | ∞ | 0.0000 | | | 2.63 |
| 32 | | ∞ | 0.2000 | | | 2.63 |
| 33 | | 9.0028 | 3.2435 | 1.8348 | 42.72 | 2.66 |
| 34 | | −12.2237 | 0.0100 | 1.5673 | 42.70 | 2.39 |
| 35 | | −12.2237 | 1.0000 | 1.7282 | 28.32 | 2.39 |
| 36 | | 5.4450 | 3.4592 | | | 2.18 |
| 37 | | 11.5448 | 6.0938 | 1.7170 | 47.98 | 2.71 |
| 38 | | −9.4890 | 0.0100 | 1.5673 | 42.70 | 2.73 |
| 39 | | −9.4890 | 10.0000 | 1.7174 | 29.50 | 2.73 |
| 40 | | 10.0707 | 0.2212 | | | 2.79 |
| 41 | | 11.0902 | 10.0000 | 1.8467 | 23.78 | 2.84 |
| 42 | | −24.9786 | 2.0000 | | | 2.79 |
| 43 | | ∞ | 0.0000 | | | 2.68 |
| 44 | | ∞ | 1.8000 | | | 2.68 |
| 45 | | 24.9786 | 10.0000 | 1.8467 | 23.78 | 2.85 |

TABLE 12

| Surface number | r | d | n | ν | Effective diameter |
|---|---|---|---|---|---|
| Object surface | ∞ | d0 | | | |
| 46 | −11.0902 | 0.2212 | | | 2.75 |
| 47 | −10.0707 | 10.0000 | 1.7174 | 29.50 | 2.71 |
| 48 | 9.4890 | 0.0100 | 1.5673 | 42.70 | 2.67 |
| 49 | 9.4890 | 6.0938 | 1.7170 | 47.98 | 2.67 |
| 50 | −11.5448 | 3.4592 | | | 2.65 |
| 51 | −5.4450 | 1.0000 | 1.7282 | 28.32 | 2.04 |
| 52 | 12.2237 | 0.0100 | 1.5673 | 42.70 | 2.17 |
| 53 | 12.2237 | 3.2435 | 1.8348 | 42.72 | 2.18 |
| 54 | 9.0028 | 0.2000 | | | 2.53 |
| 55 | ∞ | 0.0000 | | | 2.52 |
| 56 | ∞ | 0.2000 | | | 2.52 |
| 57 | 9.0028 | 3.2435 | 1.8348 | 42.72 | 2.52 |
| 58 | −12.2237 | 0.0100 | 1.5673 | 42.70 | 2.17 |
| 59 | −12.2237 | 1.0000 | 1.7282 | 28.32 | 2.17 |
| 60 | 5.4450 | 3.4592 | | | 2.00 |
| 61 | 11.5448 | 6.0938 | 1.7170 | 47.98 | 2.63 |

TABLE 12-continued

| Surface number | r | d | n | v | Effective diameter |
|---|---|---|---|---|---|
| 62 | −9.4890 | 0.0100 | 1.5673 | 42.70 | 2.71 |
| 63 | −9.4890 | 10.0000 | 1.7174 | 29.50 | 2.71 |
| 64 | 10.0707 | 0.2212 | | | 2.89 |
| 65 | 11.0902 | 10.0000 | 1.8467 | 23.78 | 2.94 |
| 66 | −24.9786 | 2.0000 | | | 2.98 |
| 67 | ∞ | 0.0000 | | | 2.76 |
| 68 | ∞ | 1.8000 | | | 2.76 |
| 69 | 24.9786 | 10.0000 | 1.8467 | 23.78 | 2.71 |
| 70 | −11.0902 | 0.2212 | | | 2.87 |
| 71 | −10.0707 | 10.0000 | 1.7174 | 29.50 | 2.84 |
| 72 | 9.4890 | 0.0100 | 1.5673 | 42.70 | 2.93 |
| 73 | 9.4890 | 6.0938 | 1.7170 | 47.98 | 2.93 |
| 74 | −11.5448 | 3.4592 | | | 2.98 |
| 75 | −5.4450 | 1.0000 | 1.7282 | 28.32 | 2.37 |
| 76 | 12.2237 | 0.0100 | 1.5673 | 42.70 | 2.56 |
| 77 | 12.2237 | 3.2435 | 1.8348 | 42.72 | 2.56 |
| 78 | −9.0028 | 0.2000 | | | 2.77 |
| 79 | ∞ | 0.0000 | | | 2.69 |
| 80 | ∞ | 0.2000 | | | 2.69 |
| 81 | 9.0028 | 3.2435 | 1.8348 | 42.72 | 2.62 |
| 82 | −12.2237 | 0.0100 | 1.5673 | 42.70 | 2.18 |
| 83 | −12.2237 | 1.0000 | 1.7282 | 28.32 | 2.17 |
| 84 | 5.4450 | 3.4592 | | | 1.94 |
| 85 | 11.5448 | 6.0938 | 1.7170 | 47.98 | 2.54 |
| 86 | 9.4890 | 0.0100 | 1.5673 | 42.70 | 2.67 |
| 87 | −9.4890 | 10.0000 | 1.7174 | 29.50 | 2.67 |
| 88 | 10.0707 | 0.2212 | | | 2.96 |
| 89 | 11.0902 | 10.0000 | 1.8467 | 23.78 | 3.02 |
| 90 | 24.9786 | 2.0000 | | | 3.15 |

TABLE 13

| Surface number | r | d | n | v | Effective diameter |
|---|---|---|---|---|---|
| Object surface | ∞ | d0 | | | |
| 91 | ∞ | 0.0000 | | | 2.95 |
| 92 | ∞ | 2.0000 | | | 2.95 |
| 93 | 16.3543 | 2.8047 | 1.8830 | 40.81 | 2.77 |
| 94 | −47.2751 | 0.2000 | | | 2.76 |
| 95 | 4.2188 | 1.5048 | 2.0010 | 29.13 | 2.69 |
| 96 | 3.5000 | 1.3549 | | | 2.16 |
| 97 | −4.8734 | 1.0000 | 1.8467 | 23.78 | 2.15 |
| 98 | 4.2417 | 0.0100 | 1.5673 | 42.70 | 2.55 |
| 99 | 4.2417 | 3.8352 | 1.8348 | 42.72 | 2.56 |
| 100 | −7.2883 | 12.5032 | | | 2.97 |
| 101 | 28.7633 | 8.4266 | 1.9229 | 20.88 | 2.42 |
| 102 | −4.6100 | 0.0100 | 1.5673 | 42.70 | 2.65 |
| 103 | −4.6100 | 1.0000 | 2.0007 | 25.46 | 2.65 |
| 104 | −16.9364 | 0.3000 | | | 2.76 |
| 105 | 7.0075 | 5.0000 | 1.8467 | 23.78 | 2.73 |
| 106 | 3.7699 | 1.8577 | | | 1.76 |
| 107 | −5.2240 | 2.0000 | 1.4970 | 81.61 | 1.91 |
| 108 | −9.6818 | 0.3000 | | | 2.40 |
| 109 | ∞ | 0.5000 | 1.9037 | 31.32 | 2.54 |
| 110 | ∞ | 1.0000 | | | 2.60 |
| 111 | ∞ | 0.0000 | | | 2.82 |
| 112 | ∞ | 1.0000 | | | 2.82 |
| 113 | 19.5400 | 1.7700 | 1.8830 | 40.81 | 3.11 |
| 114 | ∞ | 5.1949 | | | 3.17 |
| 115 | −24.7300 | 0.7000 | 1.8052 | 25.46 | 3.53 |
| 116 | 24.7300 | 0.8667 | | | 3.66 |
| 117 | −27.7000 | 1.9200 | 1.8042 | 46.50 | 3.78 |
| 118 | −16.8350 | d118 | | | 4.19 |
| 119 | 42.3300 | 3.7300 | 1.4970 | 81.61 | 7.22 |
| 120 | −25.6100 | d120 | | | 7.42 |
| 121 | −24.4000 | 1.0000 | 1.6034 | 38.01 | 7.40 |
| 122 | 24.4000 | 4.8439 | | | 7.81 |
| 123 | 33.3000 | 3.2500 | 2.0007 | 25.46 | 10.27 |
| 124 | −385.4000 | 11.0000 | | | 10.31 |
| 125 | ∞ | 4.2000 | 1.5168 | 64.20 | 10.66 |
| 126 | ∞ | 1.0000 | | | 10.84 |
| 127 | ∞ | 0.0000 | | | 10.91 |

TABLE 14

[Variable interval]

| | | | | | |
|---|---|---|---|---|---|
| d0 | ∞ | 100.0000 | 50.0000 | 25.0000 | 10.0000 |
| d118 | 11.3502 | 10.1361 | 9.0579 | 7.2054 | 3.0521 |
| d120 | 2.0561 | 3.2702 | 4.3483 | 6.2009 | 10.3542 |

[Specification table]

| | |
|---|---|
| f | 14.0166 |
| Fno. | 15.9837 |
| Optical overall length | 360.6096 |
| ω | 41.6900 |
| Y | 10.8200 |

[Focal length of each lens system/group]

| | Surface number | Focal length |
|---|---|---|
| Objective lens system | 3-19 | 3.579 |
| Relay lens system | 21-91 | 39.837 |
| Front side lens group | 92-118 | 11.274 |
| Focus group | 119-120 | 32.607 |
| Rear side lens group | 121-124 | −115.756 |
| Image forming lens system | 21-124 | −26.763 |

Example 5

(1) Configuration of Observation Optical System

Figure 9:
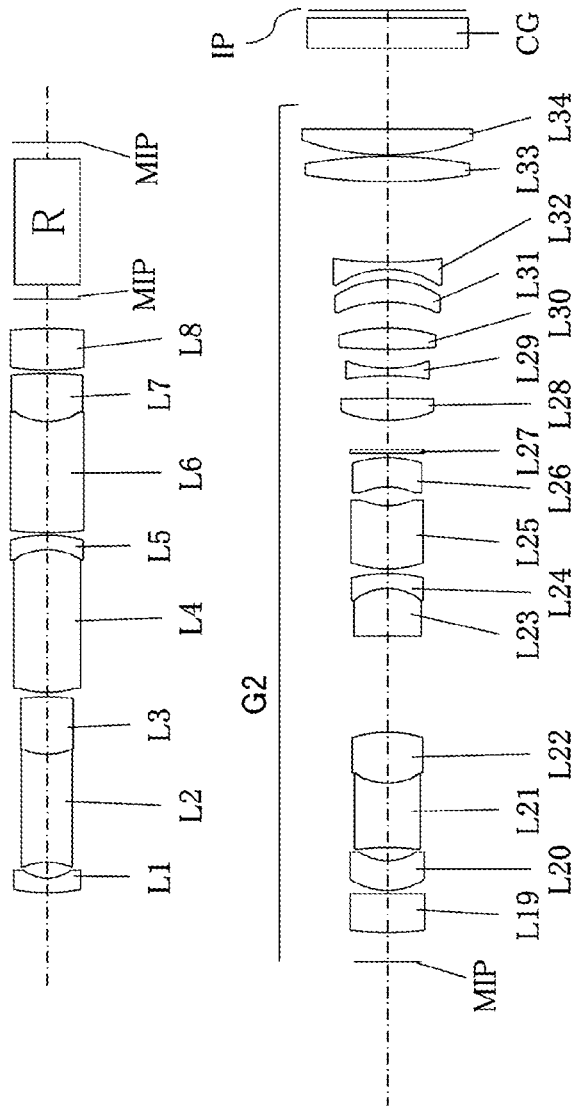
FIG. 9 is a lens sectional view of an observation optical system of example 5 according to the present invention at a time of focusing at infinity.
Figure 9:
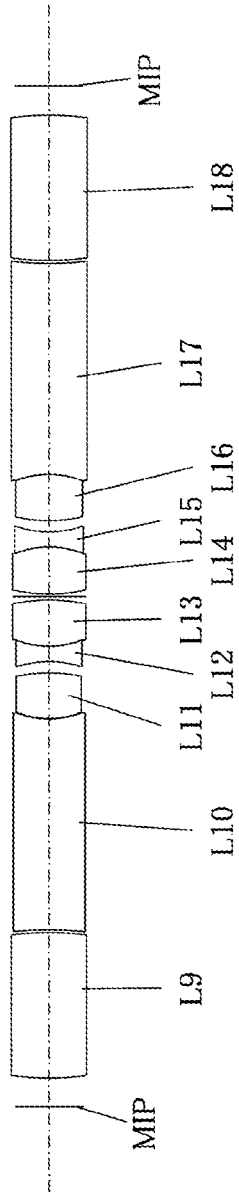

FIG. 9 shows a lens sectional view showing the lens configuration of the observation optical system according to example 5 of the present invention at a time of focusing at infinity. The observation optical system includes, from the observation object side: an objective lens system G1; and an image forming lens system G2 including a relay lens system R. In the observation optical system, an intermediate object image is formed on the first intermediate image forming plane MIP through the objective lens system G1. In the image forming lens system G2, the intermediate object image is formed on a second intermediate image forming plane MIP through the relay lens system R, and then image-formed on an image plane IP of the image sensor. The image forming lens system G2 includes not only the relay lens system R but also a focus group that moves toward the object side along the optical axis during focusing from an infinity object to a close object.

The objective lens system G1 includes, from the observation object side: a negative meniscus lens L1 with the concave surface being oriented toward the image plane side; a cemented lens including a biconcave-shaped negative lens L2 and a biconvex-shaped positive lens L3 cemented to each other; an aperture regulation surface for defining the maximum aperture; a cemented lens including a biconvex-shaped positive lens L4 and a negative meniscus lens L5 with the concave surface being oriented toward the object side; a cemented lens including a negative meniscus lens L6 with the concave surface being oriented toward the image plane side and a biconvex-shaped positive lens L7 cemented to each other; and a biconvex-shaped positive lens L8.

The image forming lens system G2 includes, sequentially from the observation object side: a relay lens system R; a biconvex-shaped positive lens L19; a negative meniscus lens L20 with the concave surface being oriented toward the image plane side; a cemented lens including a biconcave-shaped negative lens L21 and a biconvex-shaped positive lens L22 cemented to each other; a cemented lens including a positive meniscus lens L23 with the convex surface being oriented toward the image plane side and a negative meniscus lens L24 with the concave surface being oriented toward the object side which are cemented to each other; a negative meniscus lens L25 with the concave surface being oriented toward the image plane side; a negative meniscus lens L26 with the concave surface being oriented toward the object side; a parallel plate L27; a biconvex-shaped positive lens L28; a biconcave-shaped negative lens L29; a biconvex-shaped positive lens L30; a positive meniscus lens L31 with the convex surface being oriented toward the image plane side; a biconcave-shaped negative lens L32; a biconvex-shaped positive lens L33; and a positive lens L34 with the convex surface being oriented toward the object side.

As shown in FIG. 3(b), the relay lens system R includes, sequentially from the observation object side: a biconvex-shaped positive lens L9; a cemented lens including a biconcave-shaped negative lens L10 and a biconvex-shaped positive lens L11 cemented to each other; a cemented lens including a biconcave-shaped negative lens L12 and a biconvex-shaped positive lens L13 cemented to each other; a cemented lens including a biconvex-shaped positive lens L14 and a biconcave-shaped negative lens L15 cemented to each other; a cemented lens including a biconvex-shaped positive lens L16 and a biconcave-shaped negative lens L17 cemented to each other; and a biconvex-shaped positive lens L18.

In the image forming lens system G2, the lens group that includes the positive meniscus lens L31 with the convex surface being oriented toward the image plane side and the biconcave-shaped negative lens L32 is the focus group that moves toward the object side along the optical axis during focusing from an infinity object to a close object.

In this example, the image forming lens system G2 includes one relay lens system R. This example may have a configuration including multiple relay lens systems R. If the number of relay lens systems R included in the image forming lens system G2 is increased, the optical path length of the observation optical system can be increased. Consequently, the observation optical system suitable for interior observation of a narrow space that is long and thin can be obtained.

If the field curvature occurs owing to production error in this case, the occurring field curvature can be reduced by, for example, moving the relay lens system R in the optical axis direction.

If the one-side blurring occurs owing to production error, for example, the occurring one-side blurring can be reduced by integrally moving L33 and L34 included in the image forming lens system G2 in the direction perpendicular to the optical axis.

In this example, it is preferable that the pixel pitch P on the image plane IP of the image sensor range from 2 to 8 μm. The observation optical system of this example is also applicable to image sensors with pitches out of this range.

(2) Numerical Value Example

Figure 10:
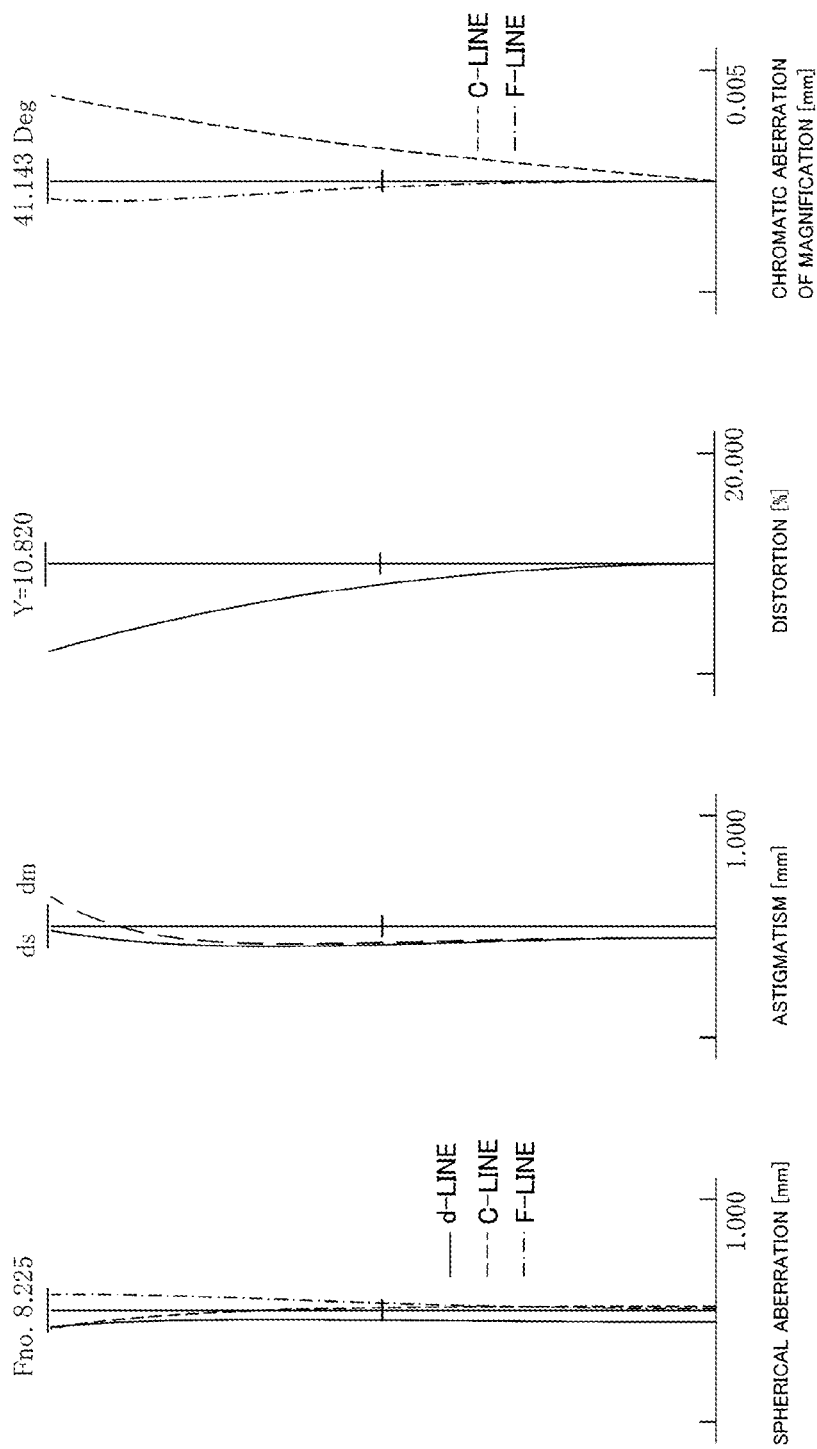
FIG. 10 is a spherical aberration diagram, an astigmatism diagram, a distortion aberration diagram, and a chromatic aberration of magnification diagram of the observation optical system according to example 5 at a time of focusing at infinity.

Next, numerical value examples where specific numerical values of the observation optical system are applied are described. Lens data on the observation optical system of this example is shown in Tables 15 and 16. Table 17 shows variable intervals on the optical axis, a specification table, and the focal length of each lens group, in the observation optical system. Furthermore, the numerical values of conditional expressions (1) to (9) are shown in Table 18. Furthermore, FIG. 10 shows longitudinal aberration diagrams of the optical system at a time of focusing at infinity.

TABLE 15

| Surface number | | r | d | n | v | Effective diameter |
|---|---|---|---|---|---|---|
| Object surface | | ∞ | d0 | | | |
| 1 | | ∞ | 0.0000 | | | 4.98 |
| 2 | | ∞ | 0.0000 | | | 4.98 |
| 3 | | 24.8000 | 2.0000 | 1.8830 | 40.81 | 4.60 |
| 4 | | 5.4000 | 2.1331 | | | 3.27 |
| 5 | | −8.8000 | 14.8400 | 1.8042 | 46.50 | 3.14 |
| 6 | | 8.8000 | 0.0200 | 1.5673 | 42.70 | 3.50 |
| 7 | | 8.8000 | 7.8800 | 1.8467 | 23.78 | 3.50 |
| 8 | S | −27.4000 | 0.6000 | | | 3.58 |
| 9 | | 14.0200 | 19.6400 | 1.5688 | 56.04 | 3.72 |
| 10 | | −7.7200 | 0.0200 | 1.5673 | 42.70 | 4.58 |
| 11 | | −7.7200 | 2.0000 | 1.8467 | 23.78 | 4.58 |
| 12 | | −18.7200 | 0.3404 | | | 4.99 |
| 13 | | 38.4000 | 15.2200 | 1.8467 | 23.78 | 5.04 |
| 14 | | 8.0000 | 0.0200 | 1.5673 | 42.70 | 4.38 |
| 15 | | 8.0000 | 6.6200 | 1.4970 | 81.61 | 4.38 |
| 16 | | −52.0000 | 0.4213 | | | 4.91 |
| 17 | | 34.8000 | 5.7200 | 1.8467 | 23.78 | 5.02 |
| 18 | | −43.5000 | 4.0008 | | | 4.97 |
| 19 | | ∞ | 0.0000 | | | 4.62 |
| 20 | | ∞ | 4.0153 | | | 4.62 |
| 21 | | 37.6600 | 20.0000 | 1.9229 | 20.88 | 5.17 |
| 22 | | −37.6600 | 0.4000 | | | 5.05 |
| 23 | | −51.2000 | 29.0200 | 1.9037 | 31.32 | 4.98 |
| 24 | | 11.7520 | 0.0200 | 1.5673 | 42.70 | 4.42 |
| 25 | | 11.7520 | 6.3800 | 1.8042 | 46.50 | 4.43 |
| 26 | | −19.0800 | 1.5443 | | | 4.46 |
| 27 | | −13.2600 | 2.0400 | 1.6990 | 30.05 | 4.20 |
| 28 | | 11.7520 | 0.0200 | 1.5673 | 42.70 | 4.54 |
| 29 | | 11.7520 | 6.5000 | 1.7440 | 44.90 | 4.54 |
| 30 | | −21.6000 | 0.4000 | | | 5.04 |
| 31 | | ∞ | 0.0000 | | | 5.04 |
| 32 | | ∞ | 0.4000 | | | 5.04 |
| 33 | | 21.6000 | 6.5000 | 1.7440 | 44.90 | 5.04 |
| 34 | | −11.7520 | 0.0200 | 1.5673 | 42.70 | 4.70 |
| 35 | | −11.7520 | 2.0400 | 1.6990 | 30.05 | 4.69 |
| 36 | | 13.2600 | 1.5443 | | | 4.39 |
| 37 | | 19.0800 | 6.3800 | 1.8042 | 46.50 | 4.59 |
| 38 | | −11.7520 | 0.0200 | 1.5673 | 42.70 | 4.51 |
| 39 | | −11.7520 | 29.0200 | 1.9037 | 31.32 | 4.51 |
| 40 | | 51.2000 | 0.4000 | | | 5.20 |

TABLE 16

| Surface number | r | d | n | v | Effective diameter |
|---|---|---|---|---|---|
| Object surface | ∞ | d0 | | | |
| 41 | 37.6600 | 20.0000 | 1.9229 | 20.88 | 5.27 |
| 42 | −37.6600 | 4.0153 | | | 5.29 |
| 43 | ∞ | 0.0000 | | | 4.68 |
| 44 | ∞ | 4.0000 | | | 4.68 |
| 45 | 38.2600 | 5.3800 | 1.8061 | 33.27 | 5.04 |
| 46 | −261.4000 | 0.4000 | | | 5.06 |
| 47 | 9.1800 | 4.1000 | 1.9229 | 20.88 | 5.05 |
| 48 | 7.0000 | 1.7817 | | | 3.91 |
| 49 | −33.6700 | 8.8400 | 1.8467 | 23.78 | 3.91 |
| 50 | 8.0000 | 0.0200 | 1.5673 | 42.70 | 4.49 |
| 51 | 8.0000 | 6.9600 | 1.8042 | 46.50 | 4.50 |
| 52 | −17.2600 | 13.2422 | | | 4.85 |
| 53 | −118.2000 | 6.5000 | 1.8052 | 25.46 | 4.07 |
| 54 | −7.0600 | 0.0200 | 1.5673 | 42.70 | 4.57 |
| 55 | −7.0600 | 2.0400 | 1.8340 | 37.35 | 4.57 |
| 56 | −19.2200 | 0.6000 | | | 4.92 |
| 57 | 14.2600 | 8.7200 | 1.9229 | 20.88 | 4.93 |
| 58 | 8.0000 | 2.6423 | | | 3.50 |

TABLE 16-continued

| Surface number | r | d | n | v | Effective diameter |
|---|---|---|---|---|---|
| 59 | −8.9600 | 4.0000 | 1.4970 | 81.61 | 3.69 |
| 60 | −14.7400 | 0.6000 | | | 4.75 |
| 61 | ∞ | 0.5000 | 1.9108 | 35.25 | 5.06 |
| 62 | ∞ | 2.0000 | | | 5.12 |
| 63 | ∞ | 0.0000 | | | 5.58 |
| 64 | ∞ | 2.0000 | | | 5.58 |
| 65 | 16.7862 | 2.9790 | 1.8830 | 40.81 | 6.31 |
| 66 | −573.7461 | 3.1604 | | | 6.17 |
| 67 | −31.8440 | 1.0000 | 1.8052 | 25.46 | 5.73 |
| 68 | 16.0133 | 2.6152 | | | 5.72 |
| 69 | 78.6384 | 2.9264 | 1.8042 | 46.50 | 6.37 |
| 70 | −23.1721 | d70 | | | 6.62 |
| 71 | −16.5000 | 3.0377 | 1.8467 | 23.78 | 6.71088 |
| 72 | −12.8019 | 1.4321 | | | 7.20421 |
| 73 | −12.2122 | 1.0000 | 1.5673 | 42.84 | 6.92426 |
| 74 | 56.2537 | d74 | | | 7.43486 |
| 75 | 73.6545 | 3.4246 | 1.4970 | 81.61 | 11.02 |
| 76 | −62.1419 | 0.2000 | | | 11.2528 |
| 77 | 34.1978 | 3.6211 | 1.4970 | 81.61 | 11.6814 |
| 78 | ∞ | 11.0000 | | | 11.6225 |
| 79 | ∞ | 4.2000 | 1.5168 | 64.20 | 11.0222 |
| 80 | ∞ | 1.0000 | | | 10.89 |
| 81 | ∞ | 0.0000 | | | 10.8462 |

TABLE 17

[Variable interval]

| d0 | ∞ | 100.0000 | 50.0000 | 30.0000 | 20.0000 |
|---|---|---|---|---|---|
| d70 | 3.5681 | 4.5876 | 5.5304 | 6.6825 | 7.9776 |
| d74 | 10.9906 | 9.9711 | 9.0284 | 7.8763 | 6.5811 |

[Specification table]

| f | 14.3603 |
|---|---|
| Fno. | 8.2251 |
| Optical overall length | 352.6963 |
| ω | 41.1430 |
| Y | 10.8200 |

[Focal length of each lens system/group]

| | Surface number | Focal length |
|---|---|---|
| Objective lens system | 3-19 | 6.298 |
| Relay lens system | 21-42 | −417.553 |
| Front side lens group | 45-70 | 46.494 |
| Focus group | 71-74 | −25.287 |
| Rear side lens group | 75-78 | 34.516 |
| Image forming lens system | 21-78 | −264.605 |

TABLE 18

| | | Example 1 | Example 2 | Example 3 | Example 4 | Example 5 |
|---|---|---|---|---|---|---|
| Conditional expression (1) | Y/P × \|β\| | 7299.3 | 12890.8 | 7299.3 | 6518.6 | 3795.3 |
| Conditional expression (2) | Y/P/Fno | 104 | 59 | 104 | 104 | 202.9 |
| Conditional expression (3) | fL1/ff | −1.297 | −1.297 | −1.331 | −1.271 | −1.297 |
| Conditional expression (4) | Nd | 1.883 | 1.904 | 2.001 | 1.883 | 1.883 |
| Conditional expression (5) | ff/\|f\| | 0.228 | 0.129 | 0.228 | 0.255 | 0.439 |
| Conditional expression (6) | \|βr\| | 0.998 | 0.998 | 1.005 | 1.015 | 0.999 |
| Conditional expression (7) | \|{(1 − (βf × βf)} × βs × βs\| | 1.543 | 2.238 | 1.508 | 1.508 | 1.924 |
| Conditional expression (8) | CrL1r/ff | 0.857 | 0.857 | 0.966 | 0.763 | 0.857 |
| Conditional expression (9) | \|β\| | 4.389 | 7.774 | 4.385 | 3.916 | 2.28 |

INDUSTRIAL APPLICABILITY

According to the present invention, a small observation optical system having a high resolution, an observation imaging device that includes the observation optical system, an observation imaging system, an image forming lens system, and a method of adjusting the observation optical system, are provided. Furthermore, the observation optical system according to the present invention is suitable for the observation imaging device, such as a microscope, for observing a minute object, or the observation imaging device for interior observation of a narrow space which no person can directly enter.

REFERENCE SIGNS LIST

G1 . . . Objective lens
G2 . . . Image forming lens
R1 . . . Relay lens R1
R2 . . . Relay lens R2
R3 . . . Relay lens R3
MIP . . . Intermediate image forming plane
IP . . . Image plane

The invention claimed is:

1. An observation optical system, comprising: an objective lens system; and an image forming lens system, sequentially from an observation object side, the image forming lens system forming an observation object image formed through the objective lens system, on an image plane of an image sensor,
wherein a following condition is satisfied, $$4000 < Y/P \times |\beta| < 32000 \quad (1)$$

where
Y: a length of half a diagonal length of the image plane,
P: a pixel pitch on the image plane, and
β: a lateral magnification of the image forming lens system.

2. The observation optical system according to claim 1, wherein a following condition is satisfied, $$50 < Y/P/Fno < 600 \quad (2)$$

where
Fno: an F number of the observation optical system.

3. The observation optical system according to claim 1, wherein a lens arranged nearest to the observation object side in the objective lens system has a negative refractive power.

4. The observation optical system according to claim 3, wherein the lens arranged nearest to the observation object side in the objective lens system satisfies a following condition, $$-3.00 < fL1/ff < -0.80 \quad (3)$$

where
fL1: a focal length of the lens arranged nearest to the observation object side in the objective lens system, and
ff: a focal length of the objective lens system.

5. The observation optical system according to claim 1, wherein the observation optical system includes at least one lens satisfying a following condition, $$1.86 < Nd \quad (4)$$

where

Nd: a refractive index for d-line.

6. The observation optical system according to claim 5, wherein the lens has a negative refractive power.

7. The observation optical system according to claim 1, wherein the lens satisfies a following condition, $$0.10 < |f7|/|f| < 0.45 \quad (5)$$

where f: a composite focal length of the observation optical system.

8. The observation optical system according to claim 1, wherein the image forming lens system comprises at least one relay lens system that forms the observation object image on an intermediate image forming plane between an image forming plane of the objective lens system and the image plane.

9. The observation optical system according to claim 8, wherein the relay lens system satisfies a following condition, $$0.9 < |\beta r| \quad (6)$$

where $\beta r$: a lateral magnification of the relay lens system.

10. The observation optical system according to claim 1, wherein the image forming lens system includes a focus group movable in an optical axis direction, and focuses by moving the focus group in the optical axis direction according to a distance to the observation object.

11. The observation optical system according to claim 10, wherein the focus group satisfies a following condition, $$0.2 < |\{(1-(\beta f \times \beta f)\} \times \beta s \times \beta s| < 12.0 \quad (7)$$

where $\beta f$: a lateral magnification of the focus group, and $\beta s$: a composite lateral magnification of the lens group arranged nearer to the image plane side than the focus group.

12. The observation optical system according to claim 1, wherein the lens arranged nearest to the observation object side in the objective lens system satisfies a following condition, $$0.70 < CrL1r/f\!f < 2.50 \quad (8)$$

where

CrL1r: a curvature radius of an image side surface of a lens arranged nearest to the observation object side in the objective lens system.

13. The observation optical system according to claim 1, wherein the objective lens system includes at least one cemented lens including a lens having a positive refractive power and a lens having a negative refractive power which are cemented to each other, and a cemented surface thereof has a negative refractive power.

14. An observation imaging device, comprising: the observation optical system according to claim 1; and the image sensor arranged on an image side of the observation optical system, wherein the image sensor converts the observation object image formed through the observation optical system into image data.

15. An observation imaging system including the observation imaging device according to claim 14, further comprising
an image processor part that electrically processes the image data pertaining to the observation object image generated by the observation imaging device.

16. The observation imaging system according to claim 15, wherein the image processor part electrically processes data pertaining to distortion aberration among the image data.

17. The observation imaging system according to claim 15, wherein the image processor part electrically processes data pertaining to chromatic aberration of magnification among the image data.

18. A method of adjusting the observation optical system according to claim 1,
wherein the method reduces an amount of error occurring owing to production error by adjusting an air interval.

19. A method of adjusting the observation optical system according to claim 1,
wherein the method reduces an amount of error occurring owing to production error by decentering at least one lens among lenses included in the observation optical system.

20. The observation optical system according to claim 1, wherein a following condition is satisfied, $$2.5 < |\beta| < 12.0 \quad (9).$$

21. An image forming lens system for forming an observation object image formed through an objective lens system, on an image plane of an image sensor,
wherein a following condition is satisfied, $$2.5 < |\beta| < 12.0 \quad (9)$$

where $\beta$: a lateral magnification of the image forming lens system; and wherein the image lens forming system includes at least one lens satisfying a following condition, $$1.86 < Nd \quad (4)$$

where

Nd: a refractive index for d-line.

* * * * *